(12) United States Patent
Illig et al.

(10) Patent No.: US 9,266,866 B2
(45) Date of Patent: Feb. 23, 2016

(54) INHIBITORS OF C-FMS KINASE

(71) Applicant: Janssen Pharmaceutica NV, Beerse (BE)

(72) Inventors: Carl R. Illig, Phoenixville, PA (US); Jinsheng Chen, Exton, PA (US); Renee Louise Desjarlais, Saint Davids, PA (US); Kenneth Wilson, Playas del Coco (CR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/210,920

(22) Filed: Mar. 14, 2014

(65) Prior Publication Data

US 2014/0200245 A1 Jul. 17, 2014

Related U.S. Application Data

(62) Division of application No. 11/736,650, filed on Apr. 18, 2007, now Pat. No. 8,722,718.

(60) Provisional application No. 60/793,667, filed on Apr. 20, 2006.

(51) Int. Cl.
| | |
|---|---|
| C07D 413/14 | (2006.01) |
| C07D 409/12 | (2006.01) |
| C07D 207/34 | (2006.01) |
| C07D 233/90 | (2006.01) |
| C07D 401/12 | (2006.01) |
| C07D 401/14 | (2006.01) |
| C07D 405/12 | (2006.01) |
| C07D 405/14 | (2006.01) |
| C07D 413/12 | (2006.01) |
| C07D 493/08 | (2006.01) |
| C07D 403/12 | (2006.01) |
| C12N 9/99 | (2006.01) |

(52) U.S. Cl.
CPC ............ *C07D 409/12* (2013.01); *C07D 207/34* (2013.01); *C07D 233/90* (2013.01); *C07D 401/12* (2013.01); *C07D 401/14* (2013.01); *C07D 403/12* (2013.01); *C07D 405/12* (2013.01); *C07D 405/14* (2013.01); *C07D 413/12* (2013.01); *C07D 413/14* (2013.01); *C07D 493/08* (2013.01); *C12N 9/99* (2013.01)

(58) Field of Classification Search
CPC .................................................. C07D 413/14
USPC ........................................ 546/271.4; 514/340
See application file for complete search history.

(56) References Cited

U.S. PATENT DOCUMENTS

| | | | |
|---|---|---|---|
| 2,466,420 A | 4/1949 | Hagemeyer et al. | |
| 3,226,394 A | 12/1965 | Schipper | |
| 4,551,540 A | 11/1985 | Hechenbleikner et al. | |
| 5,101,440 A | 3/1992 | Watanabe et al. | |
| 5,190,541 A | 3/1993 | Abele et al. | |
| 5,474,765 A | 12/1995 | Thorpe | |
| 5,534,940 A | 7/1996 | Sato et al. | |
| 5,666,164 A | 9/1997 | Kondo et al. | |
| 5,762,918 A | 6/1998 | Thorpe | |
| 5,855,866 A | 1/1999 | Thorpe et al. | |
| 5,874,442 A | 2/1999 | Doll et al. | |
| 5,940,132 A | 8/1999 | Kondo et al. | |
| 5,944,718 A | 8/1999 | Austin et al. | |
| 5,968,952 A | 10/1999 | Venet et al. | |
| 6,037,350 A | 3/2000 | Venet et al. | |
| 6,117,432 A | 9/2000 | Ganne et al. | |

(Continued)

FOREIGN PATENT DOCUMENTS

| | | |
|---|---|---|
| CN | 101017260 | 8/2007 |
| EP | 1566379 A1 | 8/2005 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*

(Continued)

*Primary Examiner* — Patricia L Morris

(57) ABSTRACT

The invention is directed to compounds of Formula I:

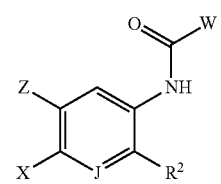

wherein Z, X, J, $R^2$ and W are set forth in the specification, as well as solvates, hydrates, tautomers and pharmaceutically acceptable salts thereof, that inhibit protein tyrosine kinases, especially c-fms kinase. Methods of treating autoimmune diseases; and diseases with an inflammatory component; treating metastasis from ovarian cancer, uterine cancer, breast cancer, prostate cancer, lung cancer, colon cancer, stomach cancer, hairy cell leukemia; and treating pain, including skeletal pain caused by tumor metastasis or osteoarthritis, or visceral, inflammatory, and neurogenic pain; as well as osteoporosis, Paget's disease, and other diseases in which bone resorption mediates morbidity including rheumatoid arthritis, and other forms of inflammatory arthritis, osteoarthritis, prosthesis failure, osteolytic sarcoma, myeloma, and tumor metastasis to bone with the compounds of Formula I, are also provided.

9 Claims, No Drawings

(56) References Cited

U.S. PATENT DOCUMENTS

| | | |
|---|---|---|
| 6,169,096 B1 | 1/2001 | Venet et al. |
| 6,187,786 B1 | 2/2001 | Venet et al. |
| 6,342,219 B1 | 1/2002 | Thorpe et al. |
| 6,420,387 B1 | 7/2002 | Venet et al. |
| 6,458,800 B1 | 10/2002 | Angibaud et al. |
| 6,596,746 B1 | 7/2003 | Das et al. |
| 6,692,491 B1 | 2/2004 | Phan |
| 6,710,781 B1 | 3/2004 | Sato |
| 6,987,119 B2 | 1/2006 | Gaiba et al. |
| 7,039,254 B1 | 5/2006 | Maenaka et al. |
| 7,157,456 B2 | 1/2007 | Straub et al. |
| 7,208,493 B2 | 4/2007 | Wrasidlo et al. |
| 7,427,683 B2 | 9/2008 | Player et al. |
| 7,429,603 B2 | 9/2008 | Player et al. |
| 7,645,755 B2 | 1/2010 | Illig et al. |
| 7,662,837 B2 | 2/2010 | Illig et al. |
| 7,790,724 B2 | 9/2010 | Player et al. |
| 7,795,279 B2 | 9/2010 | Ballentine et al. |
| 7,973,035 B2 | 7/2011 | Illig et al. |
| 2002/0016625 A1 | 2/2002 | Falotico et al. |
| 2002/0019414 A1 | 2/2002 | Altmann et al. |
| 2002/0028028 A1 | 3/2002 | Michel |
| 2002/0119962 A1 | 8/2002 | Jacobs et al. |
| 2003/0130280 A1 | 7/2003 | O'Farrell et al. |
| 2003/0153610 A1 | 8/2003 | Straub et al. |
| 2003/0169247 A1 | 9/2003 | Kawabe et al. |
| 2004/0049032 A1 | 3/2004 | Charrier et al. |
| 2005/0004112 A1 | 1/2005 | Player et al. |
| 2005/0113566 A1 | 5/2005 | Player et al. |
| 2005/0184952 A1 | 8/2005 | Konno et al. |
| 2005/0219188 A1 | 10/2005 | Kawabe et al. |
| 2006/0055661 A1 | 3/2006 | Kawaguchi |
| 2006/0100619 A1 | 5/2006 | McClurken et al. |
| 2006/0122181 A1 | 6/2006 | Ikemoto et al. |
| 2006/0132383 A1 | 6/2006 | Gally et al. |
| 2006/0148812 A1 | 7/2006 | Illig et al. |
| 2006/0189623 A1 | 8/2006 | Illig et al. |
| 2006/0258724 A1 | 11/2006 | Straub et al. |
| 2006/0281771 A1 | 12/2006 | Baumann et al. |
| 2006/0281788 A1 | 12/2006 | Baumann et al. |
| 2007/0121039 A1 | 5/2007 | Tago et al. |
| 2007/0179125 A1 | 8/2007 | Fraysse et al. |
| 2007/0182682 A1 | 8/2007 | Hong et al. |
| 2007/0249593 A1 | 10/2007 | Illig et al. |
| 2007/0259869 A1 | 11/2007 | Binch et al. |
| 2008/0051402 A1 | 2/2008 | Illig et al. |
| 2008/0068402 A1 | 3/2008 | Ioka et al. |
| 2008/0100554 A1 | 5/2008 | Mori |
| 2008/0106641 A1 | 5/2008 | Chou |
| 2008/0284719 A1 | 11/2008 | Yoshida |
| 2009/0105296 A1 | 4/2009 | Chen et al. |
| 2009/0197913 A1 | 8/2009 | Baumann et al. |
| 2011/0037785 A1 | 2/2011 | Shiomi |
| 2011/0195960 A1 | 8/2011 | Illig et al. |

FOREIGN PATENT DOCUMENTS

| | | |
|---|---|---|
| EP | 1705636 | 9/2006 |
| EP | 1936600 | 6/2008 |
| GB | 1189719 | 4/1970 |
| JP | 01/346070 | 12/2001 |
| JP | 3243861 | 1/2002 |
| JP | 02/064704 | 2/2002 |
| JP | 02/099250 | 4/2002 |
| JP | 03/255915 | 9/2003 |
| JP | 04/184937 | 7/2004 |
| JP | 04/212503 | 7/2004 |
| JP | 05/293265 | 10/2005 |
| JP | 05/309338 | 11/2005 |
| JP | 05/346639 | 12/2005 |
| JP | 06/84710 | 3/2006 |
| JP | 3766231 | 4/2006 |
| JP | 06/308665 | 11/2006 |
| JP | 07/140404 | 6/2007 |
| JP | 07/225871 | 9/2007 |
| JP | 07/310319 | 11/2007 |
| JP | 07/322944 | 12/2007 |
| JP | 08/021207 | 1/2008 |
| JP | 08/107715 | 5/2008 |
| JP | 08/116554 | 5/2008 |
| JP | 09/031585 | 2/2009 |
| JP | 08/287118 | 11/2009 |
| RU | 05/129914 | 4/2007 |
| WO | WO 94/10138 | 5/1994 |
| WO | WO 96/11932 | 4/1996 |
| WO | WO 96/21452 | 7/1996 |
| WO | WO 96/32907 | 10/1996 |
| WO | WO 97/16443 | 5/1997 |
| WO | WO 97/21701 | 6/1997 |
| WO | WO 97/30992 | 8/1997 |
| WO | WO 98/06700 | 2/1998 |
| WO | WO 98/28264 | 7/1998 |
| WO | WO 98/28303 | 7/1998 |
| WO | WO 98/40383 | 9/1998 |
| WO | WO 98/49157 | 11/1998 |
| WO | WO 98/54174 | 12/1998 |
| WO | WO 99/45712 | 9/1999 |
| WO | WO 99/45912 | 9/1999 |
| WO | WO 00/01691 | 1/2000 |
| WO | WO 00/02871 | 1/2000 |
| WO | WO 00/12498 | 3/2000 |
| WO | WO 00/12499 | 3/2000 |
| WO | WO 00/39082 | 7/2000 |
| WO | WO 01/47919 A1 | 7/2001 |
| WO | WO 02/32861 A1 | 4/2002 |
| WO | WO 02/092599 A1 | 11/2002 |
| WO | WO 03/024931 A1 | 3/2003 |
| WO | WO 03/024969 A1 | 3/2003 |
| WO | WO 03/035009 A2 | 5/2003 |
| WO | WO 03/037347 A1 | 5/2003 |
| WO | WO 03/057690 A1 | 7/2003 |
| WO | WO 03/099771 A2 | 12/2003 |
| WO | WO 03/099796 | 12/2003 |
| WO | WO 2004/005281 A1 | 1/2004 |
| WO | WO 2004/016597 A2 | 2/2004 |
| WO | WO 2004/018419 A2 | 3/2004 |
| WO | WO 2004/039782 A1 | 5/2004 |
| WO | WO 2004/043389 A2 | 5/2004 |
| WO | WO 2004/045548 | 6/2004 |
| WO | WO 2004/045549 | 6/2004 |
| WO | WO 2004/046120 A2 | 6/2004 |
| WO | WO 2004/058749 A1 | 7/2004 |
| WO | WO 2004/085388 | 10/2004 |
| WO | WO 2005/012220 | 2/2005 |
| WO | WO 2005/040139 | 5/2005 |
| WO | WO 2005/047273 | 5/2005 |
| WO | WO 2005/073225 | 8/2005 |
| WO | 2006047277 * | 5/2006 |
| WO | WO 2006/047277 A2 | 5/2006 |
| WO | WO 2006/047504 A1 | 5/2006 |
| WO | WO 2006/135630 | 12/2006 |
| WO | WO 2006/135636 | 12/2006 |
| WO | WO 2006/135713 | 12/2006 |
| WO | WO 2006/135718 | 12/2006 |
| WO | WO 2006/138155 A1 | 12/2006 |
| WO | WO 2007/048088 | 4/2007 |
| WO | WO 2009/058968 | 5/2009 |
| WO | WO 2009/157224 | 12/2009 |

OTHER PUBLICATIONS

Guillory (in Brittain ed.), "Polymorphism in Pharmaceutical Solids.," NY: Marcel Dekker, Inc., 1999, 1-2, 125-181, 183-226.*

Yu et al., "Physical characterization of, etc.," PSTT, vl. 1(3), 118-127 (1998).*

Vippagunta et al., "Crystalline Solids", Advanced Drug Delivery Reviews 48 (2001) 3-26.*

U.S. Office Action mailed Jan. 24, 2013 for corresponding U.S. Appl. No. 12/736,660.

Abstract of Japanese Patent Publication JP06-178277 published on Jun. 24, 1994.

Abarbri et al., J. Org. Chem. (2000), 65, 4618-4634.

(56) References Cited

OTHER PUBLICATIONS

Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).
Aboutaleb et al., International Sem in Surgical Oncol 6(17): 1-3, 2006.
Acute myeloid leukemia: MedlinePlus Medical Encyclopedia. Retrieved on Dec. 28, 2010. Electronic Resource: http://www.nlm.nih.gov/medlineplus/ency/article/000542.htm].
Advani, A., Curr Hematologic Malignancy Reports 1:101-107,2006.
Altman et al. The Cancer Dictionary, 1992, pp. 30-32.
Ansari-Lari, A. et al., "FLT3 mutations in myeloid sarcoma" British Journal of Haematology. Sep. 2004 126(6):785-91.
Armstrong, S.A. et al., (2004) "FLT3 mutations in childhood acute lymphoblastic leukemia." Blood. 103: 3544-6.
Arnon et al., "Monoclonal Antibodies for Immunotargeting of Drugs in Cancer Therapy", In Monoclonal Antibodies and Cancer Therapy, Reisfeld et al. (eds.), pp. 243-256 (Alan R. Liss, Inc. 1985).
Auewarakul et al., Ann Hematol, 85:108-112, 2006.
Barkenbus et al., Journal of Organic Chemistry (1951), 16, 232-8.
Baumann et al.. J Biochem Biophys Methods. 2004; 60:69-79.
Beletskaya et al., *Chem. Rev.*, 100:3009 (2000).
Beller et al., Applied Homogeneous Catalysis with Organometallic Compounds, Cornils, B. and Herrmann, W. A. (Eds.), 2, 1009-1024, VCH, Weinheim, Germany (1996).
Berenbaum et al. What is synergy? Pharmacological Reviews, 1989.
Berge, S., et al, "Pharmaceutical Salts", J. Pharm. Sci., Jan. 1977, 66(1): 1-19.
Blouin et al. Rat models of bone metastases. Clin. Exp. Metastasis, 2005, 22: 605-614.
Bodansky, M. et al., "The Practice of Peptide Synthesis", Springer-Verlag, NY (1984).
Brase et al., *Angew. Chemie Int. Ed.*, 44(33), 5188-5240, (2005).
Brase et al., Metal-Catalyzed Cross-Coupling Reactions (2nd Edition), p. 217-315, A. de Meijere, F. Diederich, Eds., Wiley-VCH, Weinheim (2004).
British Journal of Haematology, "Flt3 mutations and leukemia", 2003,122(4):523-38.
Brown et al., J. Chem. Soc., Perkin Trans. 2, 1039-1051 (2002).
Buchner T., W. Hiddemann, et al. (2002). "Acute myeloid leukemia: treatment over 60." Rev Clin Exp Hematol. 6(1):46-59.
Buchwald, E.L. et al., Top. Curr. Chem., 219:131-209 (2001).
Burnett, A. K. (2002). "Acute myeloid leukemia: treatment of adults under 60 years." Rev Clin Exp Hematol 6(1): 26-45.
Byrn et al., Solid-State Chemistry of Drugs, Second Edition, 1999, pp. 233-247.
Canibano, V. et al., Synthesis 14, 2175 (2001).
ChemBlink. Tipifarnib. Electronic Resource. Retrived on Dec. 18, 2010: [http://www.chemblink.com/products/192185-72-1.htm].
Chou TC, Talalay P. (1984) "Quantitative analysis of dose-effect relationships: the combined effects of multiple drugs or enzyme inhibitors." Adv Enzyme Regul. 22:27-55.
Clohlsy et al. Bone Cancer Pain. (Presented at the Third North American Symposium on Skeletal Complications of Malignancy, Bethesda, Maryland; Apr. 25-27, 2002).
Coll. Czech. Chem. Commun.: 31(11), 4432-41, (1966), Palecek, J.
Comprehensive Organic Transformations: Larock, R.S.; Wiley and Sons Inc., USA 1999.
Corey et al., *Tetrahedron Lett.*, 29, 995 (1988).
Cortes. Farnesyltransferase inhibitors in acute myeloid leukemia and myelodysplastic syndromes. Clinical Lymphoma, vol. 4, Suppl. 1, S30-S35, 2003.
Couturier et al., *Organic Process Research & Development*, 2002, 6, 42-48.
Crandall et al., J. Am. Chem. Soc. (1968), 90, 6251-6253.
Cummins et al., Tetrahedron (1988), 44(16), 5151.
Dib, et al., European Journal of Pharmacology. 2006, pp. 27-33, 551.
Dirlam et al., *J. Heterocyclic Chem*, 17, 409, (1980).
Dolan, S., et al, *J. Chem., Soc., Chem. Commun.*, 1588-9 (1985).

Drexler, H. G. et al. (2004), "FLT3: receptor and ligand"; Growth Factors 22(2):71-3.
Drexler, H.G., "The Leukemia-Lymphoma Cell Line Factsbook", Academic Pres:SanDiego, CA, 2000.
Eastwood, P., Tetrahedron Lett. (2000), 41, 3705-8.
Ferrara et al., "Prognostic factors and therapeutic options for relapsed or refractory acute myeloid leukemia." Haematologica. Aug. 2004, Vol. 89, No. 8, Aug. 2004; pp. 998-1008.
Fohlisch et al, *Liebigs Annalen der Chemie*, (1), 1-5 (1987) [English Abstract provided].
Galemmo et al., *J. Med. Chem.*, 33(10), 2828-41; (1990).
Gavezzotti, "Are Crystal Structures Predictable?" Accounts of Chemical Research, vol. 27, pp. 309-314 (1994).
Gilliand, G., et.al, "The roles of FLT3 in mematopoiesis and leukemia", Blood. 2002; 100:1532-42.
Gotlib, J (2005) "Farnesyltransferase inhibitor therapy in acute myelogenous leukemia." Curr. Hematol. Rep.;4(1):77-84.
Gould, P., "Salt selection for basic drugs", Ref. International J. Pharm. 1986, 33, 201-217.
Gray, M. et al., Tetrahedron Lett., 41:6237-40 (2000).
Griswold, I. J. et al., "Effects of MLN518, A Dual FLT3 and KIT inhibitor, on Normal and Malignant Hematopoiesis" Blood, Jul. 2004 [Epub ahead of print].
Guanti et al., *Tetrahedron*, 46 (20), 7081, (1990).
Guanti et al., *Tetrahedron: Asymmetry* 8(13), 2175-2187, (1997).
Haluska P., G.K. Dy, A.A. Adjei. (2002) "Farnesyl transferase inhibitors as anticancer agents." Eur J Cancer. 38(13):1685-700.
Han, J., Advances in Characterization of Pharmaceutical Hydrates, Trends in Bio/PharmaceuticalIndustry, pp. 25-29. Mar. 2006.
Harmata et al., Org. Lett. (2000), 2, 2703-2705.
Hartwig, J.F., "Organopalladium Chemistry for Organic Synthesis," Wiley Interscience, NY (2002).
Hayakawa et al., *Bioorg. Med. Chem. Lett.*, 14(2): 455-8 (2004).
Hellstrom et al., "Antibodies for Drug Delivery", in Controlled Drug Delivery (2nd Ed.), Robinson et al. (eds.), pp. 623-653 (Marcel Dekker, Inc. 1987).
Hengartner, MO. (2000) "The biochemistry of apoptosis." Nature 407:770-76.
Hess et al., J. Am. Chem. Soc. (1998), 120, 12310.
Hill et al., J. Am. Chem. Soc. (1973), 95, 1338.
Hogermeier et al., Chem. Eur. J., 2007, 13, 2410.
Hulkenberg et al., *Tetrahedron Lett.*, 23(14), 1505-08; (1982).
Iddon. B. et al., J. Chem. Soc. Perkin Trans. 1., 1370, (1980).
Illig, et al., "Discovery of novel FMS Kinase Inhibitors as Anti-inflammatory Agents" Bioorganic & Medicinal Chemistry Letters, Pergamon, 2008, pp. 1642-1648 vol. 18, No. 5.
Ishikubo et al (Jpn J Clin Oncol 36:494-498, 2006.
Itsuno et al., *Synthesis*, 12, 995-6, (1988).
Johnson et al., Brit J Cancer, 84:1424-1431 (2001).
Johnson et al., J. Org. Chem. (1970), 35(3), 584-592.
Kamwakami J., et al. "A Convenient Synthesis of 4(5)-Alkylacyl-1H-imidazoles from 4(5)-Imidazolecarboxaldehyde" Synthesis, No. 5, pp. 677-680 (2003).
Katritsky, A. et al., "*para*-Formylation of Nitroarenes via Vicarious Nucleophilic Substitution of Hydrogen with Tris(benzotriazol-1-yl)methane", Tetrahedron Lett., 37:347-50 (1996).
Khanapure et al, *J. Med. Chem.*, 48(11): 3930-34 (2005).
Kim et al., European Journal of Organic Chemistry (2000), 12, 2195-2201.
Kolder, C.R., et al, "Synthesis and Reactivity of 5-Chloro-2,4-Dihydrosypyridine", x Recl. Trav. Chim. Pays-Bas; 285 (1953).
Koutek, et al, *Synth. Commun.*, 6 (4), 305-8 (1976).
Lancet J.E., J.D. Rosenblatt, J.E. Karp. (2003) "Farnesyltransferase inhibitors and myeloid malignancies: phase I evidence of Zarnestra activity in high-risk leukemias." Semin Hematol. 39(3 Suppl 2):31-5.
Larock, R.C., Comprehensive Organic Transformations, 2$^{nd}$ Ed., Wiley-VCH, NY, (1999), pp. 996-1003.
Lee, K. and Cha, J. K., J. Amer. Chem. Soc., 123: 5590-5591 (2001).
Leonard et al., *J. Org. Chem.*, 28, 3021, (1963).
Levis, M. et al. 2001, "A FLT3 tyrosine kinase inhibitor is selectively cytoxic to acute myeloid leukemia blasts harboring FLT3 internal tandem duplication mutations", Blood 98(3):885-7.

(56) References Cited

OTHER PUBLICATIONS

Levis, M. et al., "Novel FLT3 tyrosine kinase inhibitors" Expert Opin. Investing. Drugs (2003) 12 (12) 1951-1962.
Levis, M. et al., "Small Molecule FLT3 Tyrosine Kinase Inhibitors" Current Pharmaceutical Design, 2004, 10, 1183-1193.
Levis, M., et al. (2004) "In vitro studies of a FLT3 inhibitor combined with chemotherapy: sequence of administration is important to achieve synergistic cytotoxic effects." Blood. 104(4):1145-50.
Lewis, et al. "Diacetoxypiperidinium Analogs of Acetylcholine", Junal of Medicinal Chemistry, 1973, vol. 16, No. 2 pp. 156-159.
Lipshutz et al., Tetrahedron Lett. (1988), 29, 3411-3414.
Liu et al., J. Am. Chem. Soc. 2004, 126, 5182.
Loader, C., et al, Can. J. Chem, 59, 2673 (1981).
Lovborg H, Gullbo J, Larsson R. (2005) "Screening for apoptosis-classical and emerging techniques." Anticancer Drugs 16:593-9.
Lyon, R., et al., "Synthesis and Evaluation of Phenyl-and Benzoylpiperazines as Potential Serotonergic Agents", J. Med. Chem., 29: 630-4 (1986).
Major, R., et al. "1-Alkoxy-4-phenyl-4-propionoxypiperdines and Their 3-Methyl Homologs as New Analgesics", vol. 26, pp. 1867-1847, (1961).
Martinez_Teipel et al., QSAR & Combinatorial Science, 23(10), 854-858 (2004).
McBee et al., Journal of the American Chemical Society (1957), 79, 2323-5.
McKenna, H.J. et al., "Mice lacking flt3 ligand having deficient hematopoiesis affecting hematopoietic progenitor cells, dendritic cells and natural killer cells", Blood Jun. 2000; 95:3489-3497.
Meltzer et al., Bioorganic & Medicinal Chemistry (2002), 10(11) and 3583-3591.
Miyaura, N. et al., "Palladium-Catalyzed Cross-Coupling Reactions of Organoboron Compounds", Chem. Rev. 95:2457 (1995).
Mock et al., J. Phys. Org. Chem., 16(3), 175-182 (2003).
Modern Amination Methods: Ricci, A., Ed., Wiley-VCH: Weinheim, 2000.
Muci, et al., "Practical Palladium Catalysts for C—N and C—O Bond Formation", Top. Curr., Chem. 219-131-209 (2001).
Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.
Murata, K. et al., "Synthesis of Alkenylboronates via Palladium-Catalyzed Borylation of Alkenyl Triflates (or Iodindes) with Pinacolborane" Synthesis, 2000, No. 6, pp. 778-780.
Murray, et al., "SU11248 inhibits tumor growth and CSF-1R-dependent osteolysis in an experimental breast cancer bone metastasis model", Clinical & Experimental Metastasis, 2003, pp. 757-766, vol. 20, No. 8.
Myles et al., J. Org. Chem., 55, 1636 (1990).
Nguyen et al., Tetrahedron, 62(4), 647-651; (2006).
Nicolai, E., et al., "New Process for the Synthesis of Imidazo[4-5-b]pyridine Derivatives as Potent Orally Active Thromboxane $A_2$ Receptor Antagonists", J. Heterocyclic Chemistry, 31, (73) (1994).
Nose et al., Chem. Pharm. Bull., 38(8), 2097-101, (1990).
Noyori et al., Org. React., 1983, 29, 163.
Nunez G, Benedict MA, Hu Y, Inohara N. (1998) "Caspases: the proteases of the apoptotic pathway." Oncogene 17:3237-45.
O'Farrell, A.M. et al. "SU11248 is a novel FLT3 tyrosine kinase inhibitor with potent activity in vitro and in vivo" Blood, May 2003; 101:3597-3605.
Olah, G.A. et al., "Formylating Agents", Chemical Reviews, vol. 87, No. 4, 1987.
Prendergast et al., (2001) "Farnesyl Transferase Inhibtors: Mechanism and Applications" Expert Opin Investig Drugs. 10(12):2105-16.
Protecting Groups, P, Kocienski Thieme Medical Publishers, 2000.
Pure Appl. Chem., 1976, 45:13-30.
Quentmeier H, et al. FLT3 mutations in acute myeloid leukemia cell lines. Leukemia. Jan. 2003;17:120-124.
Quintard et al., J. Org. Chem., 48: 1559-60 (1983).
Reed et al., Synthetic Communications, 20(4), 563-71, (1990).

Regan, J., et al., Structure-Activity Relationships of the p38* MAP Kinsase Inhibitor 1-)5-tert-Butyl-2-p-tolyl-2h-pyrazol-3-yl)-3-[4-(2-morpholin-4-yl-ethoxy)naph-thalen-1-yl-)urea (BIRB 796)J. Med. Chem., 46:4676-86 (2003).
Reinecke et al., Chemistry—A European Journal (1995), 1(6), 368-73.
Romeo, G., et al, "New Pyrimido [5,4-b_indoles as Ligands for *1-Adrenoceptor Subtypes", J. Med. Chem., 46: 2877-2894 (2003).
Roush, W., J. Am. Chem. Soc. 102, 1390 (1980).
Sadick, M. et al., Analysis of Heregulin-Induced ErbB2 Phosphorylation with a High-Throughput Kinase Receptor Activation Enzyme-Linked Immunsorbent Assay, Analytical Biochemistry. 1996; 235:207-214.
Sasaki et al., Tett. Lett. (1982), 23, 1693.
Sato et al., Bulletin of the Chemical Society of Japan (1983), 56(9), 2680-99.
Sato et al., Bulletin of the Chemical Society of Japan (1984), 57(9), 2515-25.
Scheijen, B. et al. (2002), "Tyrosine kinase oncogenes innormal hematopoiesis and hematological disease", Oncogene 21(21):3314-33.
Schmid et al., Helv. Chim. Acta. (1974), 57, 1883 [see English Summary provided].
Sendelbach, et al, Journal of Organic Chemistry (1999), 64(10), 3398-3408.
Shih L. Y. et al., (2004) "Internal tandem duplication of fms-like tyrosine kinase 3 is associated with poor outcome in patients with myelodysplastic syndrome." Cancer, 101; 989-98.
Simpson WG, The calcium channel blocker verapamil and cancer chemotherapy. Cell Calcium. Dec. 1985;6(6):449-67.
Smith, B. D. et al., "Single-agent CEP-701, a novel FLT3 inhibitor, shows biologic and clinical activity in patients with relapsed or refractory acute myeloid leukemia" Blood, May 2004; 103:3669-3676.
Smith, P, "The Curtius Reaction", Organic Reactions 3:337 (1947).
Stille, J.K., "The Palladium-Catalyzed Cross-Coupling Reactions of Organotin Reagents with Organic Electrophiles", Angew, Chem, Int. Ed. Engl., 25:508-524 (1986).
Stirewalt, D.L. et al. (2003), "The role of FLT3 in haematopoietic malignancies", NatRev Cancer 3(9):650-65.
Stone, R.M. et al. "PKC 412 FLT3 inhibitor therapy in AML: results of a phase II trial" An Hematol 2004; 83 Suppl 1:S89-90.
Sundermeier, U., Doebler, C. and Beller, M., Modern Oxidation Methods, Baeckvall, J. (Ed.)., 1-20, Wiley-Verlag (2004) Weinheim, Germany (2004).
Suzuki, A., "Metal-Catalyzed Coupling Reactions" F. Deiderich, P. Stang, Eds., Wiley-VCH, Weinheim (1998).
Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis."J Biol Chem 279, 26287-99.
Takahashi, K., et al, Chem. Lett. (2000), 126-7.
Takaya et al., J Amer Chem Soc, (1978), 100(6), 1765-77.
Thalhammer et al. Duration of second complete remission in patients with acute myeloid leukemia treated with chemotherapy: a retrospective single-center study. Ann. Hematology, 1996, 72: 216-222.
Thompson et al., Journal of Industrial and Engineering Chemistry (Washington, D. C.) (1952), 44,1659-62.
Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).
Tohma et al., Adv. Syn. Catalysis, 346, 111-124 (2004).
Tse, K.F. et al., "Inhibition of FLT3-mediated transformation by use of a tyrosine kinase inhibitor" Leukemia, Jul. 2001 15(7):1001-10.
van Engeland M., L.J. Nieland ,et al. (1998) "Annexin V-affinity assay: a review on an apoptosis detection system based on phosphatidylserine exposure." Cytometry. 31(1):1-9.
Walker et al, Dermatol 212:70-72, 2006 (Abstract Only).
West et al., J. Org. Chem (1993), 58, 6795-6803.
Wilson et al., Reducing Ion Channel Activity in a Series of 4-Heterocyclic Arylamide FMS Inhibitors, 20 Bioorg. & Med. Chem. Letts. 3925-3929 (2010).

(56) References Cited

OTHER PUBLICATIONS

Wroblewski et al., Journal of the American Chemical Society (1996), 118, 10168-10174.

Wustrow, et al, "Coupling of Arylboronic Acids with a Partially Reduced Pyridine Derivative" Synthesis, 993 (1991).

Wustrow et al., Tetrahedron Lett., 35, 61-4 (1994).

www.cancer.org (accessed online Mar. 2, 2010), "Can Acute Myeloid Luchemia (AML) Be Prevented?".

Yee et al. Synergistic effect of SU11248 with cytarabine or daunorubicin on FLT3 ITD-positive leukemic cells. Blood, 2004, 104: 4202-4209. Published online Aug. 10, 2004.

Yee, K.W.H. et al., "SU5416 and SU5614 inhibit kinase activity of wild-type and mutant FLT3 receptor tyrosine kinase" Blood, Sep. 2002; 100:2941-294.

Zhu et al. Farnesyltransferase inhibitor R115777 (Zarnestra, Tipifarnib) synergizes with paclitaxel to induce apoptosis and mitotic arrest and to inhibit tumor growth of multiple myeloma cells. Blood, vol. 105, No. 12, 4759-4766, Published online Feb. 22, 2005.

Chemcats RN 93730-20-2, Nov. 28, 1988.

Chemcats RN 443895-82-7 Apr. 24, 2003.

Chemcats RN 701272-70-0, Jan. 1, 2004.

Chemcats RN 712290-43, Jan. 1, 2004.

Jonas, Nilsson W. et al., "Solid-Phase Synthesis of Libraries Generated from a 4-Phenyl-2-carboxy-piperazine Scaffold", J. Comb. Chem., 2001, 3, 546-553.

Moffett, Robert Bruce et al., "Antiulcer Agents. p-Aminobenzamido Aromatic Compounds", Journal of Medicinal Chemistry, 1971, vol. 14, No. 10, pp. 963-968.

Nilsson et al., J. Comb. Chem., vol. 3, pp. 546-553 (2001).

Rastelli et al. J. Med. Chem., 2003, 46, 2834-2845.

International Search Report mailed Jan. 27, 2009 in corresponding PCT/JP2008/072403.

International Search Report mailed Jun. 9, 2009 in corresponding PCT/JP2009/054712.

International Search Report mailed Jun. 9, 2009 in corresponding PCT/JP2009/054936.

* cited by examiner

INHIBITORS OF C-FMS KINASE

CROSS REFERENCE TO RELATED APPLICATION

This application is a divisional of U.S. patent application Ser. No. 11/736,650, filed Apr. 18, 2007, pending; which claims priority to US Provisional Patent Applications 60/793,667, filed Apr. 20, 2006.

BACKGROUND OF THE INVENTION

The invention relates to novel compounds that function as protein tyrosine kinase inhibitors. More particularly, the invention relates to novel compounds that function as inhibitors of c-fms kinase.

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R overexpression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. The invention is directed to the novel compounds of Formula I:

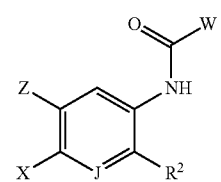

or a solvate, hydrate, tautomer or pharmaceutically acceptable salt thereof, wherein:
W is

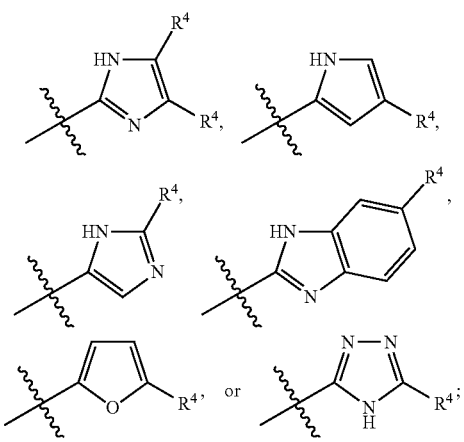

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, $C=CR^g$, or CN;
  wherein $R^d$ is H, or —$C_{(1-3)}$alkyl;
  $R^e$ is H, or —$C_{(1-3)}$alkyl;
  $R^f$ is H, or —$C_{(1-3)}$alkyl; and
  $R^g$ is H, —$CH_2OH$, or —$CH_2CH_2OH$;
$R^2$ is cycloalkyl, spiro-substituted cycloalkenyl, heterocyclyl, spirosubstituted piperidinyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl;

Z is H, F, or $CH_3$;

J is CH, or N;

X is

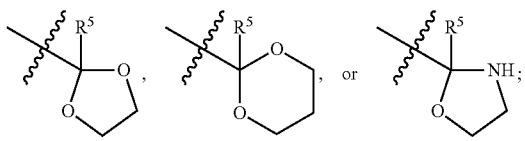

$R^5$ is H, —$C_{(1-6)}$alkyl, —$OC_{(1-4)}$alkyl, —CN, —$NA^3A^4$, —$SO_2CH_3$, —$CO_2C_{(1-4)}$alkyl, —$CH_2$—$NA^3A^4$, —$CH_2CH_2NA^3A^4$, —$CONA^3A^4$, —$CH_2OC_{(1-4)}$alkyl, —$OC_{(1-4)}$alkylOR$^a$, —$NHCH_2CH_2CO_2C_{(1-4)}$alkyl, —$NHCH_2CH_2OC_{(1-4)}$alkyl, —$N(C_{(1-4)}$alkyl)$CH_2CH_2NA^3A^4$, —$OC_{(1-4)}$alkyl$NA^3A^4$, —$OCH_2CO_2C_{(1-4)}$alkyl, —$CH_2CO_2C_{(0-4)}$alkyl, —$CH_2CH_2SO_2C_{(1-4)}$alkyl, —$SO_2CH_2CH_2NA^3A^4$, —$SOCH_2CH_2NA^3A^4$, —$SCH_2CH_2NA^3A^4$, —$NHSO_2CH_2CH_2NA^3A^4$, phenyl, imidazolyl, thiazolyl, 4H-[1,2,4]oxadiazol-5-onyl, 4H-pyrrolo[2,3-b]pyrazinyl, pyridinyl, [1,3,4]oxadiazolyl, 4H-[1,2,4]triazolyl, tetrazolyl, pyrazolyl, [1,3,5]triazinyl, and [1,3,4]thiadiazolyl;

$A^3$ is —$C_{(1-4)}$alkyl, or $CH_2CH_2OR^a$;

$A^4$ is —$C_{(1-4)}$alkyl, $COR^a$, $CH_2CON(CH_3)_2$, —$CH_2CH_2OR^a$, —$CH_2CH_2SC_{(1-4)}$alkyl, —$CH_2CH_2SOC_{(1-4)}$alkyl, or —$CH_2CH_2SO_2C_{(1-4)}$alkyl;

alternatively, $A^3$ and $A^4$ may be taken together to form a nitrogen containing heterocyclic ring selected from the following:

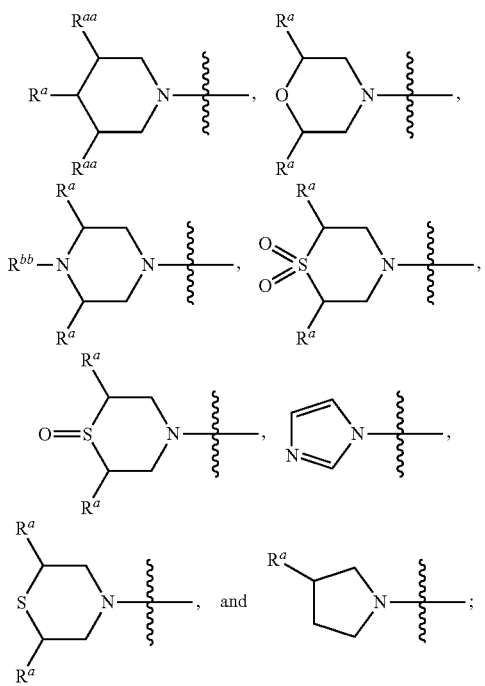

wherein $R^a$ is H or $C_{(1-4)}$alkyl;

$R^{aa}$ is H or $C_{(1-4)}$alkyl; and $R^{bb}$ is H, —$C_{(1-4)}$alkyl, —$CH_2CH_2OCH_2CH_2OCH_3$, —$CH_2CO_2H$, —$C(O)C_{(1-4)}$alkyl; or $CH_2C(O)C_{(1-4)}$alkyl.

Herein and throughout this application, whenever a variable, for example $R^a$, appears more than once in an embodiment of Formula I, each such substitution is independently defined.

Herein and throughout this application, the terms "Me", "Et", "Pr", and "Bu" refer to methyl, ethyl, propyl, and butyl respectively.

DETAILED DESCRIPTION OF THE INVENTION

The invention is directed to novel compounds of Formula I:

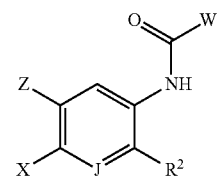

I or a solvate, hydrate, tautomer or pharmaceutically acceptable salt thereof, wherein:

W is

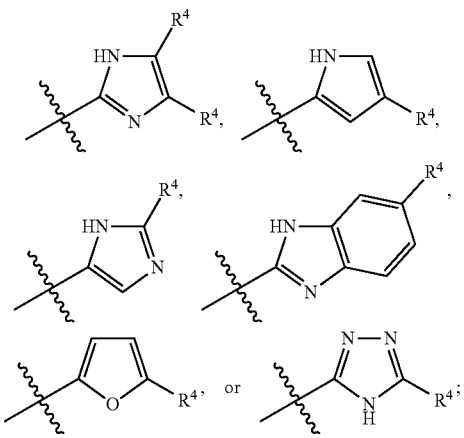

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, $C$=$CR^g$, or CN;

wherein $R^d$ is H, or —$C_{(1-3)}$alkyl;

$R^e$ is H, or —$C_{(1-3)}$alkyl;

$R^f$ is H, or —$C_{(1-3)}$alkyl; and $R^g$ is H, —$CH_2OH$, or —$CH_2CH_2OH$;

$R^2$ is cycloalkyl (including cyclohexenyl, and cycloheptenyl), spiro-substituted cycloalkenyl (including spiro[2.5]oct-5-enyl, spiro[3.5]non-6-enyl, spiro[4.5]dec-7-enyl, and spiro[5.5]undec-2-enyl)heterocyclyl (including piperidinyl), spirosubstituted piperidinyl (including 3-aza-spiro[5.5]undecanyl, and 8-aza-spiro[4.5]decanyl), thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl (said substituted cycloalkyls include 4,4-dimethyl cyclohexenyl, 4,4-diethyl cyclohexenyl, 4-methyl cyclohexenyl, 4-ethyl cyclohexenyl, 4-n-propyl cyclohexenyl, 4-iso-propyl cyclohexenyl, and 4-tert-butyl cyclohexenyl; said substituted piperidinyls include 4-methyl piperidinyl, 4-ethyl piperidinyl, 4-(1'hydroxyeth-2'yl)piperidinyl, and 4,4 dimethyl piperidinyl);

Z is H, F, or CH$_3$;

J is CH, or N;

X is

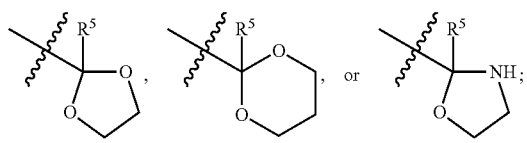

R$^5$ is H, —C$_{(1-6)}$alkyl, —OC$_{(1-4)}$alkyl, —CN, —NA$^3$A$^4$, —SO$_2$CH$_3$, —CO$_2$C$_{(1-4)}$alkyl, —CH$_2$—NA$^3$A$^4$, —CH$_2$CH$_2$NA$^3$A$^4$, —CONA$^3$A$^4$, —CH$_2$OC$_{(1-4)}$alkyl, —OC$_{(1-4)}$alkylOR$^a$, —NHCH$_2$CH$_2$CO$_2$C$_{(1-4)}$alkyl, —NHCH$_2$CH$_2$OC$_{(1-4)}$alkyl, —N(C$_{(1-4)}$alkyl)CH$_2$CH$_2$NA$^3$A$^4$, —OC$_{(1-4)}$alkylNA$^3$A$^4$, —OCH$_2$CO$_2$C$_{(1-4)}$alkyl, —CH$_2$CO$_2$C$_{(1-4)}$alkyl, —CH$_2$CH$_2$SO$_2$C$_{(1-4)}$alkyl, —SO$_2$CH$_2$CH$_2$NA$^3$A$^4$, —SOCH$_2$CH$_2$NA$^3$A$^4$, —SCH$_2$CH$_2$NA$^3$A$^4$, —NHSO$_2$CH$_2$CH$_2$NA$^3$A$^4$, phenyl, imidazolyl, thiazolyl, 4H-[1,2,4]oxadiazol-5-onyl, 4H-pyrrolo[2,3-b]pyrazinyl, pyridinyl, [1,3,4]oxadiazolyl, 4H-[1,2,4]triazolyl, tetrazolyl, pyrazolyl, [1,3,5]triazinyl, and [1,3,4]thiadiazolyl;

A$^3$ is —C$_{(1-4)}$alkyl, or CH$_2$CH$_2$OR$^a$;

A$^4$ is —C$_{(1-4)}$alkyl, COR$^a$, CH$_2$CON(CH$_3$)$_2$, —CH$_2$CH$_2$OR$^a$ (including —CH$_2$CH$_2$OCH$_3$), —CH$_2$CH$_2$SC$_{(1-4)}$alkyl (including —CH$_2$CH$_2$SCH$_3$), —CH$_2$CH$_2$SOC$_{(1-4)}$alkyl (including —CH$_2$CH$_2$SOCH$_3$), or —CH$_2$CH$_2$SO$_2$C$_{(1-4)}$alkyl (including —CH$_2$CH$_2$SO$_2$CH$_3$);

alternatively, A$^3$ and A$^4$ may be taken together to form a nitrogen containing heterocyclic ring selected from the following:

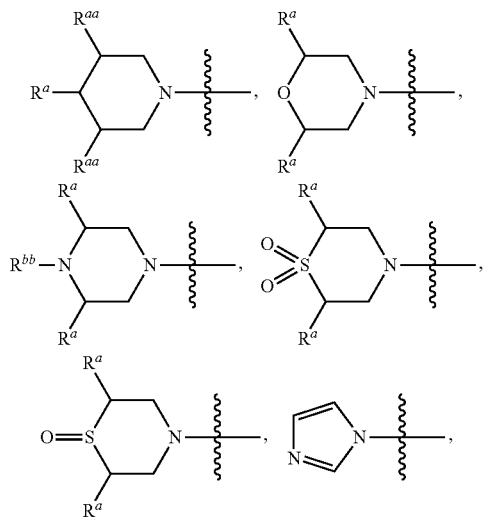

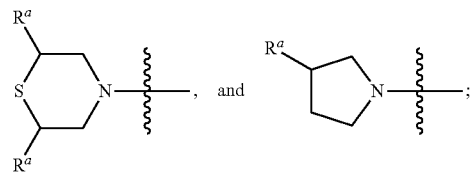

wherein R$^a$ is H or C$_{(1-4)}$alkyl;

R$^{aa}$ is H or C$_{(1-4)}$alkyl; and

R$^{bb}$ is H, —C$_{(1-4)}$alkyl, —CH$_2$CH$_2$OCH$_2$CH$_2$OCH$_3$, —CH$_2$CO$_2$H, —C(O)C$_{(1-4)}$alkyl; or CH$_2$C(O)C$_{(1-4)}$alkyl;

and solvates, hydrates, tautomers and pharmaceutically acceptable salts thereof.

In a preferred embodiment of the invention:

W is

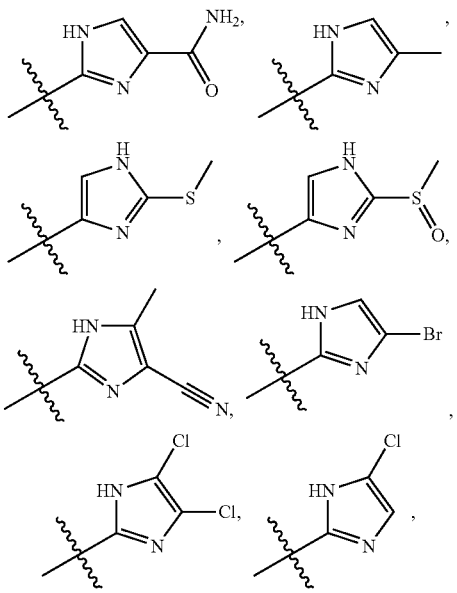

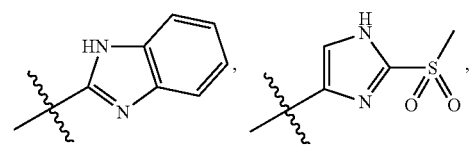

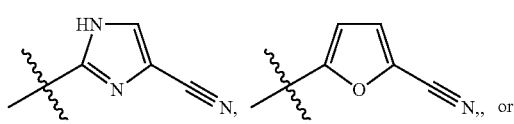

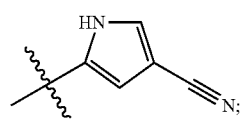

R² is

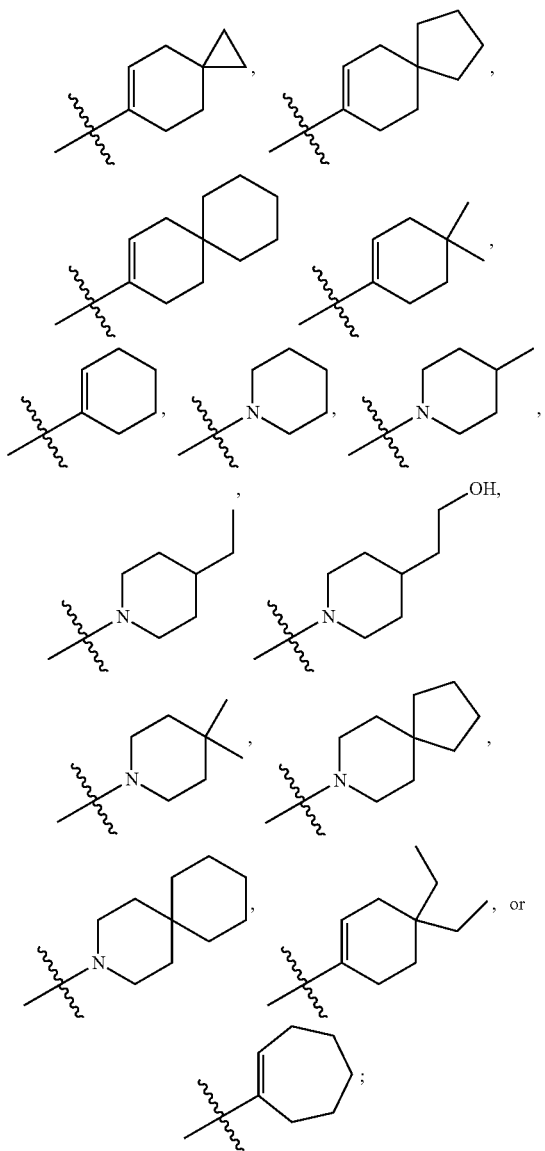

Z is H;
J is CH or N;
X is

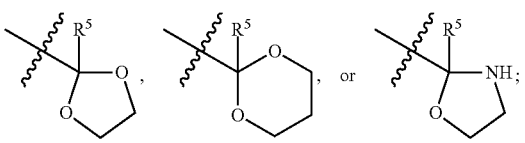

R⁵ is H, —C₍₁₋₆₎alkyl, phenyl, —CH₂CH₂NA³A⁴, —CH₂CH₂SO₂CH₃, pyridyl, imidazolyl, —CH₂NA³A⁴, or —CH₂ORᵃ;
wherein:
A³ is —CH₃;
A⁴ is —COCH₃, or —CH₃;

alternatively, A³ and A⁴ may be taken together to form a nitrogen containing heterocyclic ring selected from the following:

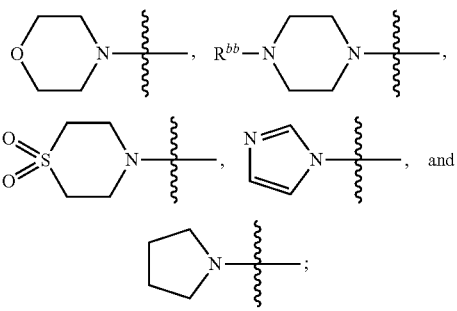

Rᵃ is H, or —C₍₁₋₄₎alkyl;
Rᵇᵇ K is —C₍₁₋₄₎alkyl, or —COCH₃;
as well as solvates, hydrates, tautomers and pharmaceutically acceptable salts thereof.

In another embodiment of the invention:
W is

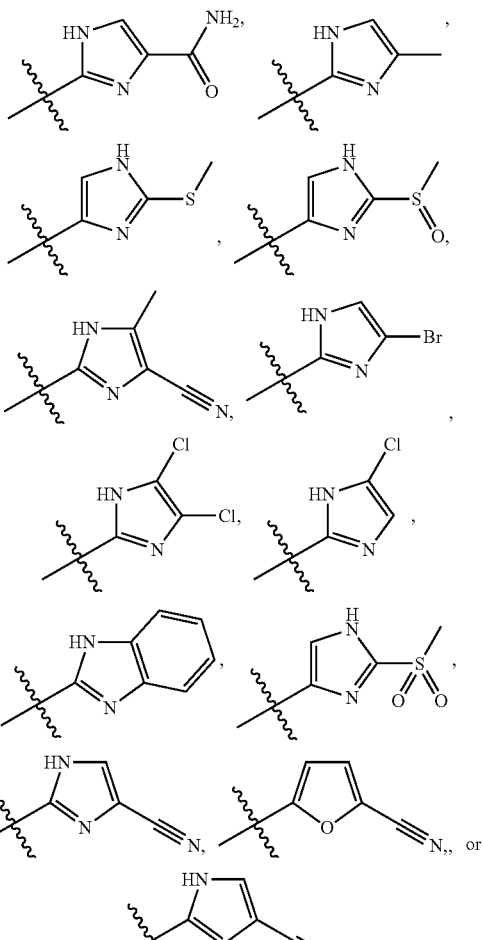

$R^2$ is

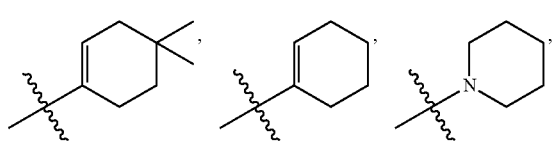

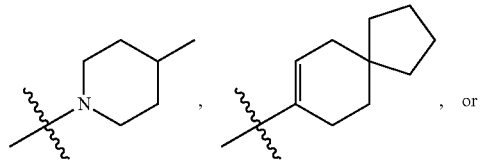

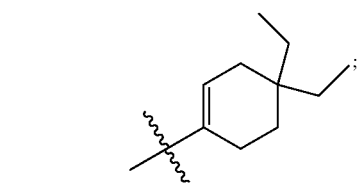

J is CH, or N;
X is

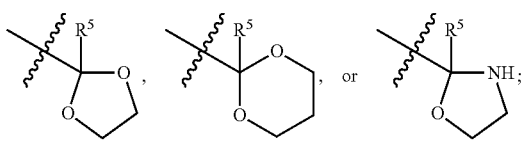

$R^5$ is —$C_{(1-3)}$alkyl, —$CH_2NA^3A^4$, or —$CH_2OR^a$;
  wherein:
  $A^3$ is —$CH_3$;
  $A^4$ is —$COCH_3$, or —$CH_3$;
  alternatively, $A^3$ and $A^4$ may be taken together to form a nitrogen containing heterocyclic ring selected from the following:

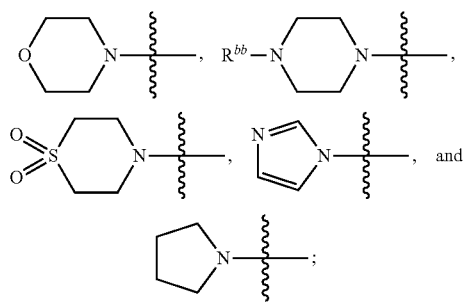

$R^a$ is H, or —$C_{(1-4)}$alkyl;
  $R^{bb}$ is —$C_{(1-4)}$alkyl, or —$COCH_3$;
as well as solvates, hydrates, tautomers and pharmaceutically acceptable salts thereof.

In another embodiment of the invention:
W is

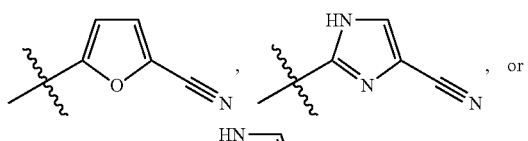

$R^2$ is

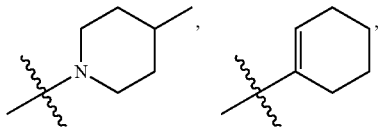

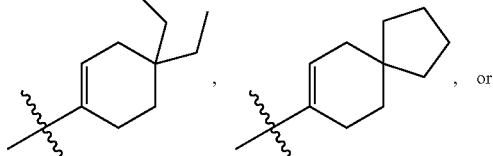

Z is H;
J is CH, or N;
X is

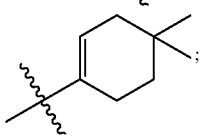

as well as solvates, hydrates, tautomers and pharmaceutically acceptable salts thereof.

In another embodiment of the invention:
W is

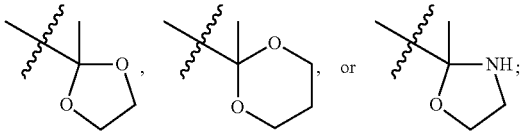

$R^2$ is

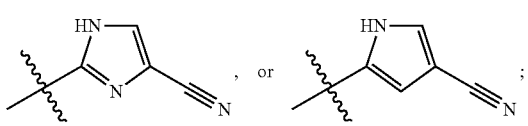 [SMILES: *c1nc(C#N)c[nH]1 ; *c1cc(C#N)c[nH]1]

Z is H;
J is CH, or N;

X is

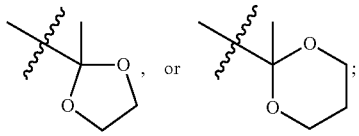

as well as solvates, hydrates, tautomers and pharmaceutically acceptable salts thereof.

In another embodiment of the invention:
W is

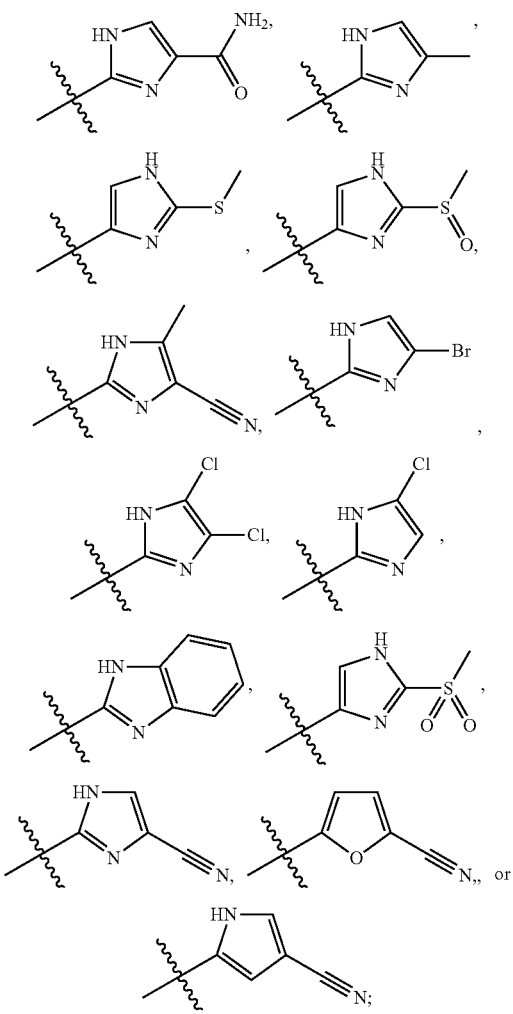

R² is

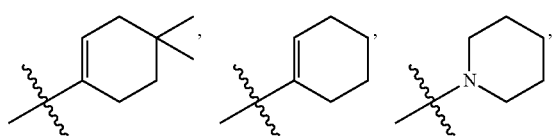

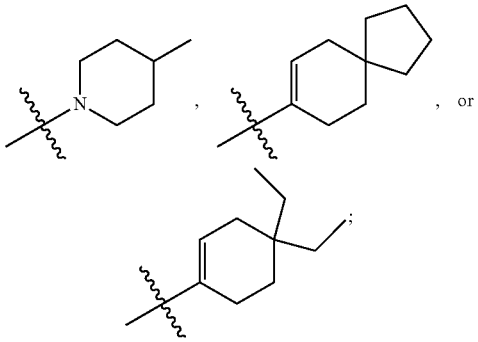

Z is H;
J is CH, or N;
X is

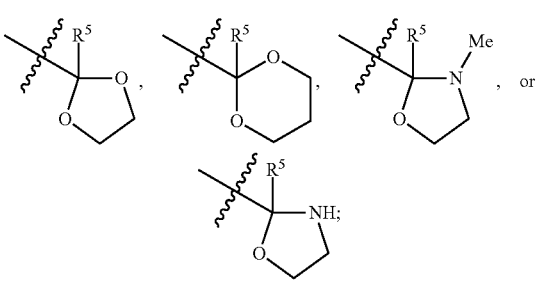

R⁵ is —C$_{(1-3)}$alkyl, —CH$_2$NA³A⁴, or —CH$_2$OR$^a$;
  wherein:
   A³ is —CH$_3$;
   A⁴ is —COCH$_3$, or —CH$_3$;
   alternatively, A³ and A⁴ may be taken together to form a nitrogen containing heterocyclic ring selected from the following:

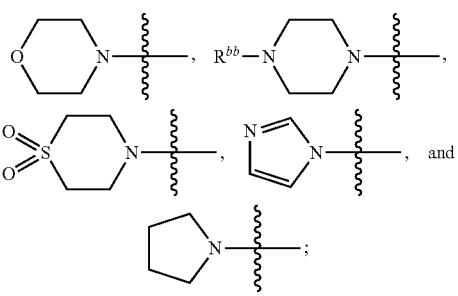

R$^a$ is H, or —C$_{(1-4)}$alkyl;
R$^{bb}$ is —C$_{(1-4)}$alkyl, or —COCH$_3$;
as well as solvates, hydrates, tautomers and pharmaceutically acceptable salts thereof.
and pharmaceutically acceptable salts thereof solvates, hydrates, tautomers and pharmaceutically acceptable salts thereof.

Another embodiment of the invention consists of example numbers 1, 2, 3, 4, 5, and solvates, hydrates, tautomers and pharmaceutically acceptable salts thereof, and any combination thereof.

The invention also relates to methods of inhibiting protein tyrosine kinase activity in a mammal by administration of a therapeutically effective amount of at least one compound of Formula I. A preferred tyrosine kinase is c-fms.

The invention is considered to include the enantiomeric, diastereomeric and tautomeric forms of all compounds of Formula I as well as their racemic mixtures. In addition, some of the compounds represented by Formulae I may be prodrugs, i.e., derivatives of an acting drug that possess superior delivery capabilities and therapeutic value as compared to the acting drug. Prodrugs are transformed into active drugs by in vivo enzymatic or chemical processes.

I. DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2, 3-trimethylcyclopentyl, cyclohexyl, cyclopentenyl, cyclohexenyl, and 4,4-dimethyl cyclohexenyl.

The term "alkylamino" refers to an amino with one alkyl substituent, wherein the amino group is the point of attachment to the rest of the molecule.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "spiro-substituted cycloalkenyl" refers to a pair of cycloalkyl rings that share a single carbon atom and wherein at least one of the rings is partially unsaturated, for example:

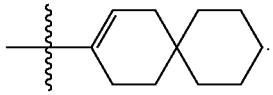

The term "spiro-substituted heterocyclyl" refers to a heterocyclyl and cycloalkyl ring that share a single carbon atom, for example:

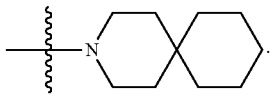 [SMILES: *N1CCC2(CCCCC2)CC1]

II. THERAPEUTIC USES

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. The compounds of the present invention are also inhibitors of FLT3 tyrosine kinase activity. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, acute myeloid leukemia, acute lymphocytic leukemia, ovarian cancer, uterine cancer, prostate cancer, lung cancer, breast cancer, colon cancer, stomach cancer, and hairy cell leukemia. The invention also provides methods of treating certain precancerous lesions including myelofibrosis. In one embodiment of the invention, an effective amount of at least one compound of Formula I is administered in combination with an effective amount of a chemotherapeutic agent.

The invention further provides methods of treating and of preventing metastasis arising from cancers that include, but are not limited to, ovarian cancer, uterine cancer, prostate cancer, lung cancer, breast cancer, colon cancer, stomach cancer, and hairy cell leukemia.

The invention further provides methods for the treatment osteoporosis, Paget's disease, and other diseases in which bone resorption mediates morbidity including rheumatoid arthritis and other forms of inflammatory arthritis, osteoarthritis, prosthesis failure, osteolytic sarcoma, myeloma, and tumor metastasis to bone as occurs frequently in cancers including, but not limited to, breast cancer, prostate cancer, and colon cancer.

The invention also provides methods of treating pain, in particular skeletal pain caused by tumor metastasis or osteoarthritis, as well as visceral, inflammatory, and neurogenic pain.

The invention also provides methods of treating cardiovascular, inflammatory, and autoimmune diseases in mammals, including humans, by administration of a therapeutically effective amount of a pharmaceutically acceptable form of at least one of the compounds of Formula I. Examples of diseases with an inflammatory component include glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia or Alzheimer's dementia. These may be effectively treated with compounds of this invention. Other diseases that may be effectively treated include, but are not limited to atherosclerosis and cardiac hypertrophy.

Autoimmune diseases such as systemic lupus erythematosus, rheumatoid arthritis, and other forms of inflammatory arthritis, psoriasis, Sjogren's syndrome, multiple sclerosis, or uveitis, can also be treated with compounds of this invention.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

Methods of Preparation

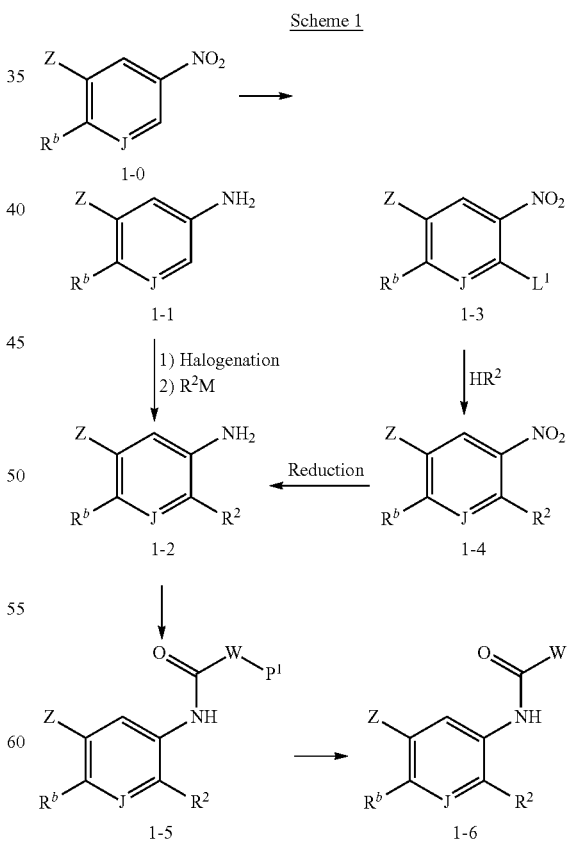

Scheme 1 illustrates general methodology for the preparation of compounds of Formula I where $R^b$ is X (when X is available in starting material or prepared as shown in later schemes) or compounds of Formula 1-6 where $R^b$ is a leaving group (preferably bromo, chloro, or fluoro) that are useful intermediates used in later schemes. To illustrate the methodology of this scheme, reagents and conditions for the compounds where J is CH are defined. Those skilled in the art will recognize that where J is N, minor modifications of the reaction conditions and preferred reagents may be required.

Amines of Formula 1-1 may be commercially available or can be obtained from nitro compounds of Formula 1-0 by reduction using standard synthetic methodology (see Reductions in Organic Chemistry, M. Hudlicky, Wiley, New York, 1984). The preferred conditions are catalytic hydrogenation using a palladium catalyst in a suitable solvent such as methanol or ethanol. In cases where $R^b$ is a halogen and not available as amines of Formula 1-1, nitro reductions may be performed using iron or zinc in a suitable solvent such as acetic acid, or using iron and ammonium chloride in ethanol and water.

Compounds of Formula 1-2 where $R^2$ is cycloalkyl can be obtained by ortho-halogenation, preferably bromination, of amino compounds of Formula 1-1 followed by metal-catalyzed coupling reactions with boronic acids or boronate esters (Suzuki reactions, where $R^2M$ is $R^2B(OH)_2$ or a boronic ester, see N. Miyaura and A. Suzuki, *Chem. Rev.*, 95:2457 (1995); A. Suzuki in Metal-Catalyzed Coupling Reactions, F. Deiderich, P. Stang, Eds., Wiley-VCH, Weinheim (1988)) or tin reagents (Stille reactions, where $R^2M$ is $R^2Sn(alkyl)_3$, see J. K. Stille, *Angew. Chem., Int. Ed. Engl.*, 25: 508-524 (1986)) on the intermediate halo compound. When $R^b$ is Br, an iodo can be introduced such that is reacts preferentially over the bromine in the metal-catalyzed coupling reactions (when J is CH, this compound is commercially available). Preferred conditions for the bromination of 1-1 are N-bromosuccinimide (NBS) in a suitable solvent such as N,N-dimethylformamide (DMF), dichloromethane (DCM) or acetonitrile. Metal-catalyzed couplings, preferably Suzuki reactions, can be performed according to standard methodology, preferably in the presence of a palladium catalyst such as tetrakis(triphenylphosphine)palladium(0) $(Pd(PPh_3)_4)$, an aqueous base such aq. $Na_2CO_3$, and a suitable solvent such as toluene, ethanol, 1,4-dioxane, dimethoxyethane (DME), or DMF.

Compounds of Formula 1-2 where $R^2$ is cycloalkylamino (for example, piperidino) can be obtained by nucleophilic aromatic substitution of leaving groups $L^1$ (preferably fluoro or chloro) from compounds of Formula 1-3 that are activated by the nitro group with cycloalkylamines ($R^2H$; for example, piperidine) in the presence of a suitable base such as $K_2CO_3$, N,N-diisopropylethylamine (DIEA) or $NEt_3$ to give compounds 1-4, followed by reduction of the nitro group as described above.

The amino group in compounds of Formula 1-2 can then be coupled with a heterocyclic acid $P^1$—WCOOH (or a corresponding salt thereof $P^1$—WCOOM$^2$, where $M^2$ is Li, Na or K) where $P^1$ is an optional protecting group (for example 2-(trimethylsilyl)ethoxymethyl (SEM) such as when W is imidazole, triazole, pyrrole, or benzimidazole) or where $P^1$ is not present such as when W is furan. (For a list of protecting groups for W, see Theodora W. Greene and Peter G. M. Wuts, Protective Groups in Organic Synthesis, John Wiley and Sons, Inc., NY (1991)). The coupling can be carried out according to standard procedures for amide bond formation (for a review, see: M. Bodansky and A. Bodansky, The Practice of Peptide Synthesis, Springer-Verlag, NY (1984)) or by reaction with acid chlorides $P^1$—WCOCl or activated esters $P^1$—WCO$_2R^q$ (where $R^q$ is a leaving group such as pentafluorophenyl or N-succinimide) to form compounds of Formula 1-5. The preferred reaction conditions for coupling with $P^1$—WCOOH or $P^1$—WCOOM$^2$ are: when W is a furan (optional protecting group $P^1$ not present), oxalyl chloride in dichloromethane (DCM) with DMF as a catalyst to form the acid chloride WCOCl and then coupling in the presence of a trialkylamine such as N,N-diisopropylethylamine (DIEA); when W is a pyrrole (optional protecting group $P^1$ not present), 1-(3-dimethylaminopropyl)-3-ethylcarbodiimide hydrochloride (EDCI) and 1-hydroxybenzotriazole (HOBt); and when W is an imidazole, pyrrole or benzimidazole (optional $P^1$ present) the preferred conditions are bromotripyrrolidinophosphonium hexafluorophosphate (PyBroP) and DIEA in a solvent such as DCM or DMF.

When W in compounds of Formula 1-5 contain an optional protecting group $P^1$ as mentioned previously, it can be removed at this point to give compounds of Formula 1-6. For example, when W is imidazole protected on nitrogen with a SEM group, the SEM group can be removed with either acidic reagents such as trifluoroacetic acid (TFA) or fluoride sources such as tetrabutylammonium fluoride (TBAF) (see Greene and Wuts above).

Finally it is understood that in compounds of Formula I (i.e., Formula 1-6 where $R^b$ is X) may be further derivatized. Examples of further derivatization, include, but are not limited to: when compounds of Formula I contain a cyano group, this group may be hydrolyzed to amides or acids under acidic or basic conditions; when compounds of Formula I contain an ester, the ester may be hydrolysed to the acid, and the acid may be converted to amides by the methods described above for amide bond formation. Amides may be converted to amines by a Curtius or Schmidt reaction (for review see, *Angew. Chemie Int. Ed.*, 44(33), 5188-5240, (2005)) or amines may be obtained by reduction of cyano groups (*Synthesis*, 12, 995-6, (1988) and *Chem. Pharm. Bull.*, 38(8), 2097-101, (1990)). Acids may be reduced to alcohols, and alcohols may be oxidized to aldehydes and ketones. The preferred conditions for the reduction of a carboxylic acid in the presence of a cyano group include sodium borohydride and ethyl chloroformate in tetrahydrofuran (THF); and alcohol oxidation can be performed using the Dess-Martin periodinane reagent (*Adv. Syn. Catalysis*, 346, 111-124 (2004)). Aldehydes and ketones may be reacted with primary or secondary amines in the presence of a reducing agent such as sodium triacetoxyborohydride (see *J. Org. Chem.*, 61, 3849-3862, (1996)) to give amines by reductive amination. Olefins may be reduced by catalytic hydrogenation. When compounds of Formula I contain a sulfide, either acyclic or cyclic, the sulfide can be further oxidized to the corresponding sulfoxides or sulfones. Sulfoxides can be obtained by oxidation using an appropriate oxidant such as one equivalent of meta-chloroperbenzoic acid (MCPBA) or by treatment with $NaIO_4$ (see, for example, *J. Med. Chem.*, 46: 4676-86 (2003)) and sulfones can be obtained using two equivalents of MCPBA or by treatment with 4-methylmorpholine N-oxide and catalytic osmium tetroxide (see, for example, PCT application WO 01/47919). Also, both sulfoxides and sulfones can be prepared by using one equivalent and two equivalents of $H_2O_2$ respectively, in the presence of titanium (IV) isopropoxide (see, for example, *J. Chem. Soc., Perkin Trans.* 2, 1039-1051 (2002)).

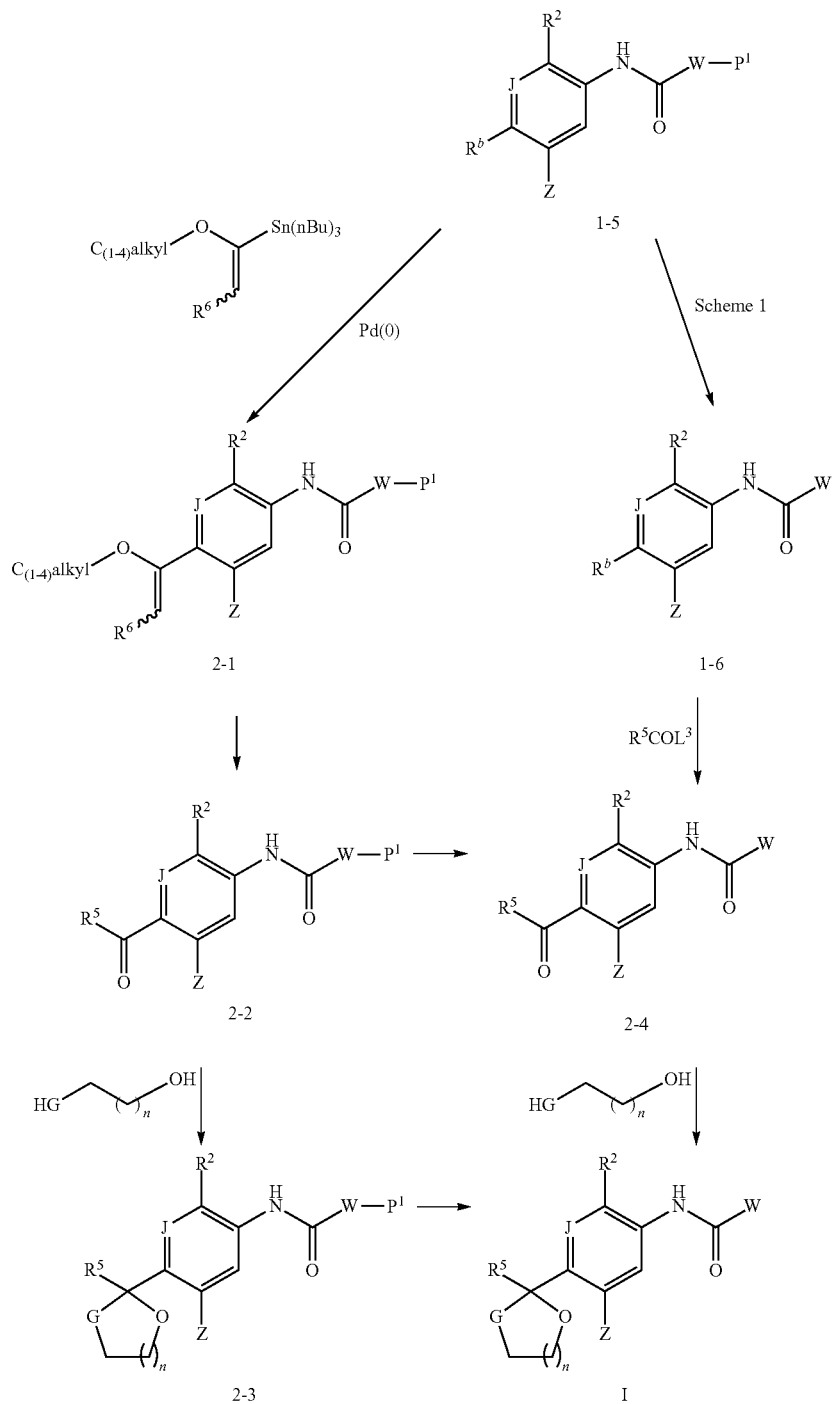

Scheme 2 illustrates the synthesis of compounds of Formula I where X is

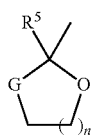

and G is O (where n is 1-2) or NR$^a$ (where n is 1).

For the illustration of synthetic strategy in this scheme, reagents and conditions are defined for the substrate where J is CH. It is understood that similar synthetic methods can be utilized with minor modifications when J is N.

The starting material, compound 1-5 (R$^b$ is Br), is obtained as described in Scheme 1. Its optional protecting group P$^1$, if present, can be removed at this point as described in Scheme 1 to give compound 1-6 which can also serve as a starting material in this synthetic sequence.

Bromide 1-5 can be subjected to a Stille coupling with an alkoxyvinyltin reagent (where $R^6$ is H, $C_{1-5}$alkyl, $OC_{(1-4)}$alkyl, $NA^3A^4$, $CH_2NA^3A^4$, $CO_2C_{(1-4)}$alkyl, $CH_2SO_2C_{(1-4)}$alkyl) as shown (see, for example, *J. Org. Chem.*, 48: 1559-60 (1983)) to give compound 2-1. The vinyl alkyl ether group ($C_{(1-4)}$alkylOC=CH($R^6$)—) in compound 2-1 can be hydrolyzed by acidic reagents, such as trifluoroacetic acid or acetic acid, to afford the ketone 2-2 (where =CH—$R^6$ becomes —$R^5$). Optional protecting group $P^1$, if stable to the hydrolysis conditions, can also be removed at this point to give 2-4 as described in Scheme 1.

Alternatively 2-4 can be obtained directly from 1-6 by reaction of an organolithium intermediate (as derived in Scheme 4 for the conversion of 1-6 to 4-1) with an appropriate electrophile $R^5COL^3$ such as an acid chloride (where $L^3$ is Cl; see, for example, *J. Med. Chem.*, 48, 3930-34 (2005)) or a Weinreb amide (where $L^3$ is N(OMe)Me; see, for example, *Bioorg. Med. Chem. Lett.*, 14(2): 455-8 (2004)).

The ketone 2-4 can be converted to a 5- or 6-membered ring ketal of Formula I where G is O and n is 1-2 (see Protective Groups in Organic Synthesis, T. H. Greene and Peter G. M. Wuts, John Wiley and Sons, NY (1991)) or to a 5-membered ring aminal of Formula I where G is $NR^a$ and n is 1 (see Bergmann, E. D., *Chem. Rev.*, 309-352 (1953) and Gosain, R., et al, *Tetrahedron Lett.*, 40, 6673-6 (1999)). The 5- or 6-membered ring ketals (G is O) are synthesized from 1,2-ethanediol (where n is 1) or 1,3-propanediol (where n is 2), using an appropriate acid catalyst, preferably para-toluenesulfonic acid, in an anhydrous solvent, preferably benzene or toluene.

Similarly, optionally protected compound 2-2, when $P^1$ is chosen such that it is stable to the ketal- and aminal-forming conditions, can also be converted to ketals or aminals 2-3 as just described and then deprotected as described in Scheme 1 to provide the compound of Formula I.

It is understood that functional groups of compounds in this scheme can be further derivatized as outlined in Scheme 1.

Scheme 3

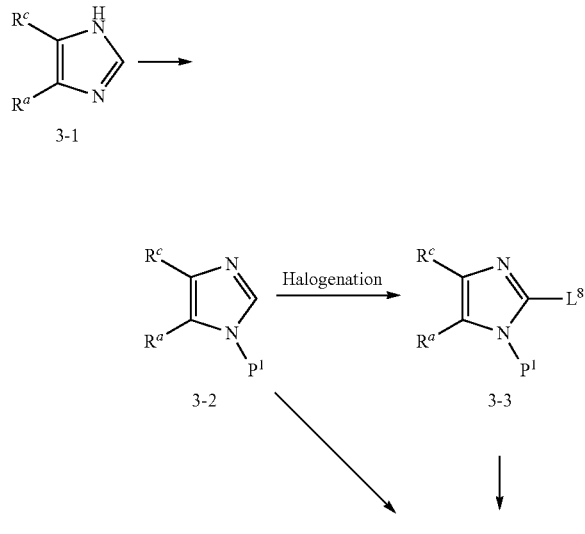

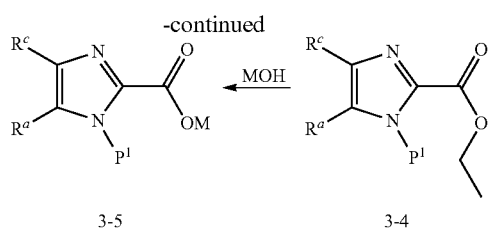

Scheme 3 illustrates a route to the preparation of 2-imidazolecarboxylates of Formula 3-5 where $R^a$ is H or $C_{(1-4)}$alkyl, and $R^d$ is H, alkyl, —CN, or —$CONH_2$ that are used as intermediates in the synthesis of compounds of Formula I where W is imidazole.

Imidazoles of Formula 3-1 where $R^a$ is H or $C_{(1-4)}$alkyl, and $R^c$ is H, $C_{(1-4)}$alkyl or —CN are either commercially available or, in the case where $R^c$ is —CN, are readily available from commercially available aldehydes (3-1 where $R^c$ is CHO) by reaction with hydroxylamines followed by dehydration with a suitable reagent such as phosphorus oxychloride or acetic anhydride (*Synthesis*, 677, 2003). Imidazoles of Formula 3-1 are protected with a suitable group ($P^1$) such as a methoxymethylamine (MOM), or preferably a SEM group to give compounds of Formula 3-2 (see Theodora W. Greene and Peter G. M. Wuts, Protective Groups in Organic Synthesis, John Wiley and Sons, Inc., NY (1991)).

Imidazoles of Formula 3-2, where $R^c$ is —CN, are halogenated with a suitable reagent such as N-bromosuccinimide or N-iodosuccinimide under either electrophilic conditions in a solvent such as DCM or $CH_3CN$ or under radical conditions in the presence of an initiator such as azobis(isobutyronitrile) (AIBN) in a solvent such as $CCl_4$ to give compounds of Formula 3-3 where $L^8$ is a leaving group (preferably bromo or iodo). Halogen-magnesium exchange on compounds of Formula 3-3 provides the organomagnesium species, which is then reacted with a suitable electrophile to provide compounds of Formula 3-4. The preferred conditions for halogen-magnesium exchange are using an alkyl-magnesium reagent, preferably isopropylmagnesium chloride in a suitable solvent such as THF at temperatures between –78° C.- to 0° C. The preferred electrophiles are ethyl chloroformate or ethyl cyanoformate. For examples of halogen-magnesium exchange on cyanoimidazoles see *J. Org. Chem.* 65, 4618, (2000).

For imidazoles of Formula 3-2, where $R^c$ is not —CN, these may be converted directly to imidazoles of Formula 3-4 by deprotonation with a suitable base such as an alkyllithium followed by reaction with an electrophile as described above for the organomagnesium species. The preferred conditions are treating the imidazole with n-butyllithium in THF at –78° C. and quenching the resulting organolithium species with ethyl chloroformate (for examples, see *Tetrahedron Lett.*, 29, 3411-3414, (1988)).

The esters of Formula 3-4 may then be hydrolyzed to carboxylic acids (M is H) or carboxylate salts (M is Li, Na, or K) of Formula 3-5 using one equivalent of an aqueous metal hydroxide (MOH) solution, preferably potassium hydroxide in a suitable solvent such as ethanol or methanol. Synthesis of compounds of Formula 3-5 where $R^d$ is —$CONH_2$ is accomplished by first treating compounds of Formula 3-4 where $R^c$ is —CN with an appropriate alkoxide such as potassium ethoxide to convert the cyano group to an imidate group (Pinner reaction) followed by hydrolysis of both the ester and imidate groups with two equivalents of an aqueous metal hydroxide solution.

Scheme 4

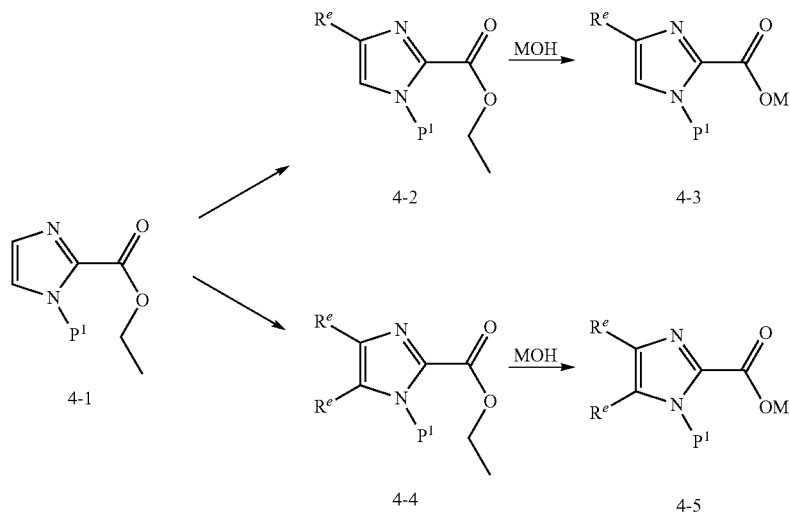

Scheme 4 illustrates a route to 2-imidazolecarboxylates of Formula 4-3 or 4-5 where $R^e$ is chloro or bromo, and M is H, Li, K, or Na that are used as intermediates in the synthesis of compounds of Formula I where W is imidazole.

Compounds of Formula 4-1 are first prepared by protection of commercially available ethyl imidazolecarboxylate according to the methods outlined in Scheme 8, preferably with a SEM group.

Compounds of Formula 4-2 are prepared by reaction of compounds of Formula 4-1 with one equivalent of an appropriate halogenating reagent, such as NBS or NCS in a suitable solvent such as $CH_3CN$, DCM or DMF at 25° C. Compounds of Formula 4-4 are prepared by reaction of compounds of Formula 4-1 with two equivalents of an appropriate halogenating reagent, such as NBS or NCS in a suitable solvent such as $CH_3CN$ or DMF at temperatures between 30° C. to 80° C. Imidazoles of Formula 4-3 and 4-5 are then obtained from the respective esters by hydrolysis as described in Scheme 3.

Scheme 5

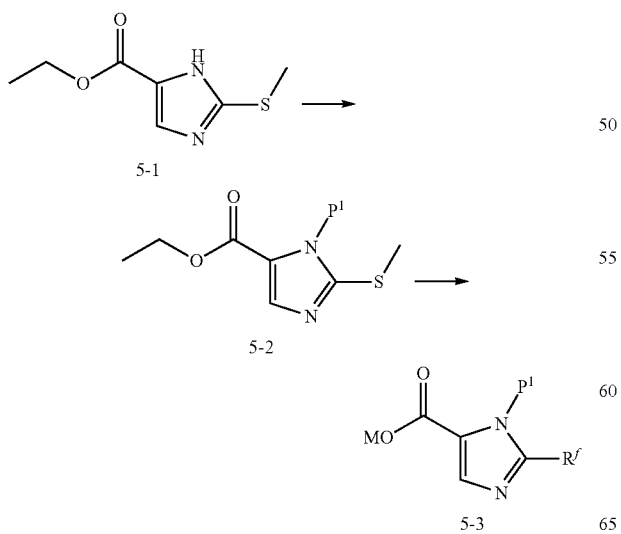

Scheme 5 illustrates a method for the preparation of imidazoles of Formula 5-3 where $R^f$ is $—SCH_3$, $—SOCH_3$, or $—SO_2CH_3$, M is H, Li, K, or Na that are used as intermediates in the synthesis of compounds of Formula I where W is imidazole.

Imidazole 5-1 (WO 1996011932) is protected according to the methods described in Scheme 3, preferably with a SEM protecting group to give compounds of Formula 5-2. Ester hydrolysis according to the procedure in Scheme 3 gives compounds of Formula 5-3 where $R^f$ is $—SCH_3$. Oxidation of 2-methylthioimidazoles of Formula 5-2 with one equivalent of an appropriate oxidant, followed by ester hydrolysis according to the procedure in Scheme 3 gives compounds of Formula 5-3 where $R^f$ is $—SOCH_3$. Oxidation with two equivalents of an appropriate oxidant, followed by ester hydrolysis according to the procedure in Scheme 3 gives compounds of Formula 5-3 where $R^f$ is $—SO_2CH_3$. The preferred reagent for oxidation is MCPBA in DCM. References for the conversion of sulfides to sulfoxides and sulfones are given in Scheme 1.

The following examples are for exemplary purposes only and are in no way meant to limit the invention.

Example 1

5-Cyano-1H-imidazole-2-carboxylic acid [2-cyclohex-1-enyl-4-(2-methyl-[1,3]dioxolan-2-yl)-phenyl]-amide

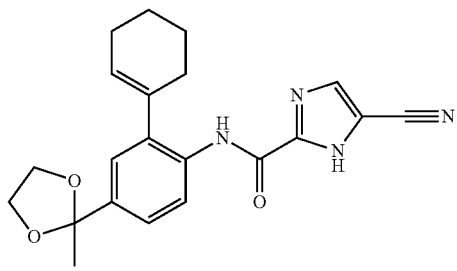 [SMILES: CC1(c2ccc(NC(=O)c3ncc(C#N)[nH]3)c(C3=CCCCC3)c2)OCCO1]

a) 1-(2-Trimethylsilanyl-ethoxymethyl)-1H-imidazole-4-carbonitrile

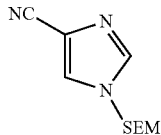 [SMILES: C[Si](C)(C)CCOCn1cnc(C#N)c1]

A flask charged with imidazole-4-carbonitrile (0.50 g, 5.2 mmol) (*Synthesis*, 677, 2003), 2-(trimethylsilyl)ethoxymethyl chloride (SEMCl) (0.95 mL, 5.3 mmol), $K_2CO_3$ (1.40 g, 10.4 mmol), and acetone (5 mL) was stirred for 10 h at RT. The mixture was diluted with EtOAc (20 mL), washed with water (20 mL), brine (20 mL) and the organic layer was dried over $MgSO_4$. The crude product was eluted from a 20-g solid phase extraction (SPE) cartridge (silica) with 30% EtOAc/hexane to give 0.80 g (70%) of the title compound as a colorless oil. Mass spectrum ($CI(CH_4)$, m/z): Calcd. for $C_{10}H_{17}N_3OSi$, 224.1 (M+H). found 224.1.

b) 2-Bromo-1-(2-trimethylsilanyl-ethoxymethyl)-1H-imidazole-4-carbonitrile

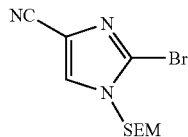

To a solution of 1-(2-trimethylsilanyl-ethoxymethyl)-1H-imidazole-4-carbonitrile (0.70 g, 3.1 mmol) (as prepared in the previous step) in $CCl_4$ (10 mL) was added N-bromosuccinimide (NBS) (0.61 g, 3.4 mmol) and azobis(isobutyronitrile) (AIBN) (cat), and the mixture was heated at 60° C. for 4 h. The reaction was diluted with EtOAc (30 mL), washed with $NaHCO_3$ (2×30 mL), brine (30 mL), the organic layer was dried over $Na_2SO_4$ and then concentrated. The title compound was eluted from a 20-g SPE cartridge (silica) with 30% EtOAc/hexane to give 0.73 g (77%) of a yellow solid. Mass spectrum ($CI(CH_4)$, m/z): Calcd. for $C_{10}H_{16}BrN_3OSi$, 302.0/304.0 (M+H). found 302.1/304.1.

c) 4-Cyano-1-(2-trimethylsilanyl-ethoxymethyl)-1H-imidazole-2-carboxylic acid ethyl ester

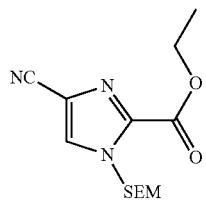 [SMILES: CCOC(=O)c1nc(C#N)cn1COCC[Si](C)(C)C]

To a solution of 2-bromo-1-(2-trimethylsilanyl-ethoxymethyl)-1H-imidazole-4-carbonitrile (0.55 g, 1.8 mmol) (as prepared in the previous step) in tetrahydrofuran (THF) (6 mL) at −40° C. was added dropwise a solution of 2 M i-PrMgCl in THF (1 mL). The reaction was allowed to stir for 10 min at −40° C. and then cooled to −78° C., and ethyl cyanoformate (0.30 g, 3.0 mmol) was added. The reaction was allowed to attain RT and stirred for 1 h. The reaction was quenched with saturated aq $NH_4Cl$, diluted with EtOAc (20 mL), washed with brine (2×20 mL). The organic layer was dried over $Na_2SO_4$ and then concentrated. The title compound was eluted from a 20-g SPE cartridge (silica) with 30% EtOAc/hexane to give 0.40 g (74%) of a colorless oil. Mass spectrum (ESI, m/z): Calcd. for $C_{13}H_{21}N_3O_3Si$, 296.1 (M+H). found 296.1.

d) 4-Cyano-1-(2-trimethylsilanyl-ethoxymethyl)-1H-imidazole-2-carboxylate potassium salt

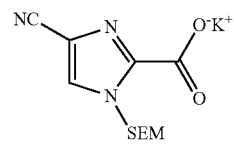

To a solution of 4-cyano-1-(2-trimethylsilanyl-ethoxymethyl)-1H-imidazole-2-carboxylic acid ethyl ester (0.40 g, 1.3 mmol) (as prepared in the previous step) in ethanol (3 mL) was added a solution of 6M KOH (0.2 mL, 1.2 mmol) and the reaction was stirred for 10 min and then concentrated to give 0.40 g (100%) of the title compound as a yellow solid. $^1$H-NMR ($CD_3OD$; 400 MHz) δ 7.98 (s, 1H), 5.92 (s, 2H), 3.62 (m, 2H), 0.94 (m, 2H), 0.00 (s, 9H). Mass spectrum (ESI-neg, m/z): Calcd. for $C_{11}H_{16}KN_3O_3Si$, 266.1 (M-K). found 266.0.

e) 4-Bromo-2-cyclohex-1-enyl-phenylamine

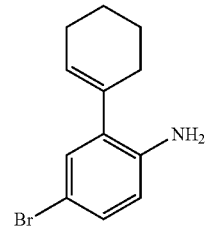 [SMILES: Nc1ccc(Br)cc1C1=CCCCC1]

To a mixture of 4-bromo-2-iodo-phenylamine (2.00 g, 6.71 mmol), 2-cyclohex-1-enyl-4,4,5,5-tetramethyl-[1,3,2]dioxaborolane (1.40 g, 6.71 mmol) and $Pd(PPh_3)_4$ (388 mg, 0.336 mmol) in 40 mL of 1,4-dioxane was added 2.0 M aq $Na_2CO_3$ solution (26.8 mL, 53.7 mmol). After stirring at 80° C. for 5 h under Ar, the reaction was cooled to RT. The mixture was treated with EtOAc (100 mL), washed with $H_2O$ (3×30 mL) and brine (20 mL). The organic layer was dried ($Na_2SO_4$) and concentrated in vacuo. The residue was purified by flash chromatography on silica gel (10-20% EtOAc/hexane) to give 1.47 g (87%) of the title compound as a light brown oil. Mass spectrum (ESI, m/z): Calcd. for $C_{12}H_{14}BrN$, 252.0 (M+H). found 252.0.

f) 4-Cyano-1-(2-trimethylsilanyl-ethoxymethyl)-1H-imidazole-2-carboxylic acid (4-bromo-2-cyclohex-1-enyl-phenyl)-amide

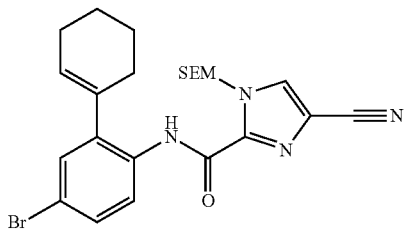 [SMILES: C[Si](C)(C)CCOCn1cc(C#N)nc1C(=O)Nc1ccc(Br)cc1C1=CCCCC1]

To a mixture of 4-bromo-2-cyclohex-1-enyl-phenylamine (as prepared in the previous step, 1.23 g, 4.88 mmol), potassium 4-cyano-1-(2-trimethylsilanyl-ethoxymethyl)-1H-imidazole-2-carboxylate (as prepared in Example 1, step (d), 1.49 g, 4.88 mmol) and PyBroP (2.27 g, 4.88 mmol) in 25 mL of DMF was added N,N-diisopropylethylamine (DIEA) (2.55 mL, 14.6 mmol). After stirring at RT for 16 h, the mixture was treated with 100 mL of EtOAc and washed with $H_2O$ (2×30 mL), brine (30 mL) and dried ($Na_2SO_4$). The organic solvent was evaporated and the residue was purified by flash chromatography on silica gel (5-10% EtOAc/hexane) to give 2.21 g (90%) of the title compound as a white solid. $^1$H-NMR (CDCl$_3$; 400 MHz): δ 9.70 (s, 1H), 8.26 (d, 1H, J=8.6 Hz), 7.78 (s, 1H), 7.36 (dd, 1H, J=8.6, 2.3 Hz), 7.31 (d, 1H, J=2.3 Hz), 5.94 (s, 2H), 5.86 (m, 1H), 3.66 (t, 2H, J=8.3 Hz), 2.19-2.33 (m, 4H), 1.75-1.88 (m, 4H), 0.97 (t, 2H, J=8.3 Hz), 0.00 (s, 9H).

g) 4-Cyano-1-(2-trimethylsilanyl-ethoxymethyl)-1H-imidazole-2-carboxylic acid (4-acetyl-2-cyclohex-1-enyl-phenyl)-amide

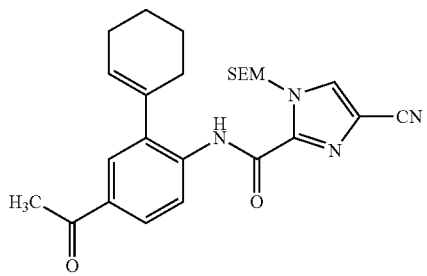 [SMILES: CC(=O)c1ccc(NC(=O)c2nc(C#N)cn2COCC[Si](C)(C)C)c(C2=CCCCC2)c1]

A mixture of 4-cyano-1-(2-trimethylsilanyl-ethoxymethyl)-1H-imidazole-2-carboxylic acid (4-bromo-2-cyclohex-1-enyl-phenyl)-amide (as prepared in the previous step, 100 mg, 0.199 mmol), tributyl(1-ethoxyvinyl)stannane (86.3 mg, 0.239 mmol) and Pd(PPh$_3$)$_2$Cl$_2$ (10.5 mg, 0.0149 mmol) in 2 mL of 1,4-dioxane was stirred at 90° C. for 2 h under Ar. After cooling to RT, the reaction was treated with EtOAc (40 mL) and washed with 15% citric acid aqueous solution (2×10 mL), $H_2O$ (10 mL) and brine (10 mL). The organic layer was dried over $Na_2SO_4$ and concentrated in vacuo. The residue was purified by flash chromatography on silica gel (10-20% EtOAc/hexane) to give 80.1 mg (86%) of the title compound as a light brown oil. Mass spectrum (ESI, m/z): Calcd. for $C_{25}H_{32}N_4O_3Si$, 465.2 (M+H). found 465.1.

h) 4-Cyano-1-(2-trimethylsilanyl-ethoxymethyl)-1H-imidazole-2-carboxylic acid [2-cyclohex-1-enyl-4-(2-methyl-[1,3]dioxolan-2-yl)-phenyl]-amide

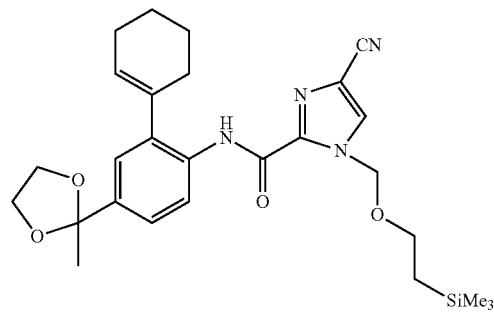 [SMILES: CC1(c2ccc(NC(=O)c3nc(C#N)cn3COCC[Si](C)(C)C)c(C3=CCCCC3)c2)OCCO1]

A solution of 4-cyano-1-(2-trimethylsilanyl-ethoxymethyl)-1H-imidazole-2-carboxylic acid (4-acetyl-2-cyclohex-1-enyl-phenyl)-amide (as prepared in the previous step, 135 mg, 0.290 mmol), ethanediol (363 mg, 5.80 mmol) and catalytic p-toluenesulfonic acid (PTSA) in 21 mL of benzene were heated at reflux under Dean-Stark conditions for 4 h. The reaction was diluted with EtOAc (25 mL), washed with water (3×20 mL), dried ($Na_2SO_4$), and concentrated in vacuo. Purification of the residue using preparative TLC (10% MeOH—CHCl$_3$) afforded 100 mg (68%) of the title compound as a white solid. Mass spectrum (ESI, m/z): Calcd. for $C_{27}H_{36}N_4O_4Si$, 509.2 (M+H). found 509.0.

i) 5-Cyano-1H-imidazole-2-carboxylic acid [2-cyclohex-1-enyl-4-(2-methyl-[1,3]dioxolan-2-yl)-phenyl]-amide To a solution of 4-cyano-1-(2-trimethylsilanyl-ethoxymethyl)-1H-imidazole-2-carboxylic acid [2-cyclohex-1-enyl-4-(2-methyl-[1,3]dioxolan-2-yl)-phenyl]-amide (as prepared in the previous step, 45 mg, 0.088 mmol) in 3 mL of THF was added tetrabutyl ammonium fluoride (TBAF) (69 mg, 0.264 mmol). The reaction was stirred for 14 h at room temperature, at which time the temperature was raised to 60° C. for 15 min and then diluted with EtOAc (25 mL) and washed with water (3×25 mL). The organic layer was dried ($Na_2SO_4$) and concentrated in vacuo. Purification of the residue using preparative TLC (10% MeOH—CHCl$_3$) afforded 31 mg (93%) of the title compound as a white solid. $^1$H-NMR (CDCl$_3$; 400 MHz): δ 9.76 (s, 1H), 8.28 (s, 1H), 7.97 (d, 1H, J=8.3 Hz), 7.33 (dd, 1H, J=8.3, 2.0 Hz), 7.21 (s, 1H, J=2.0 Hz), 5.77 (s, 1H), 3.98 (m, 2H), 3.72 (m, 2H), 2.20-2.15 (m, 4H), 1.75-1.66

(m, 4H), 1.56 (s, 3H). Mass spectrum (ESI, m/z): Calcd. for C$_{21}$H$_{22}$N$_4$O$_3$, 379.1 (M+H). found 379.1.

Example 2

4-Cyano-1H-imidazole-2-carboxylic acid [2-cyclohex-1-enyl-4-(2-methyl-[1,3]dioxan-2-yl)-phenyl]-amide

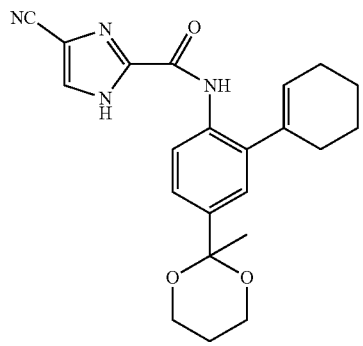 [SMILES: CC1(c2ccc(NC(=O)c3nc(C#N)c[nH]3)c(C3=CCCCC3)c2)OCCCO1]

a) 4-Cyano-1-(2-trimethylsilanyl-ethoxymethyl)-1H-imidazole-2-carboxylic acid [2-cyclohex-1-enyl-4-(2-methyl-[1,3]dioxan-2-yl)-phenyl]-amide

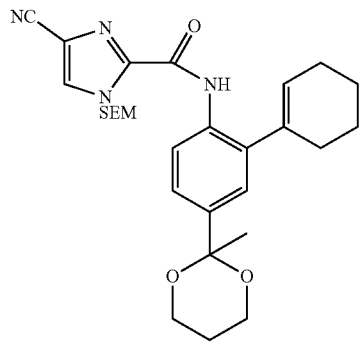 [SMILES: CC1(c2ccc(NC(=O)c3nc(C#N)cn3COCC[Si](C)(C)C)c(C3=CCCCC3)c2)OCCCO1]

The title compound was prepared from 4-cyano-1-(2-trimethylsilanyl-ethoxymethyl)-1H-imidazole-2-carboxylic acid (4-acetyl-2-cyclohex-1-enyl-phenyl)-amide (as prepared in Example 1, step (h), 0.58 mmol), 1,3-propanediol (882 mg, 11.6 mmol) and catalytic PTSA according to the procedure in Example 1, step (h) (147 mg, 49%). Mass spectrum (ESI, m/z): Calcd. for C$_{28}$H$_{38}$N$_4$O$_4$Si, 523.2 (M+H). found 523.3.

b) 4-Cyano-1H-imidazole-2-carboxylic acid [2-cyclohex-1-enyl-4-(2-methyl-[1,3]dioxan-2-yl)-phenyl]-amide The title compound was prepared from 4-cyano-1-(2-trimethylsilanyl-ethoxymethyl)-1H-imidazole-2-carboxylic acid [2-cyclohex-1-enyl-4-(2-methyl-[1,3]dioxan-2-yl)-phenyl]-amide (as prepared in the previous step, 145 mg, 0.276 mmol) and tetrabutylammonium fluoride (216 mg, 0.820 mmol) according to the procedure in Example 1, step (i) (69.4 mg, 64%). $^1$H-NMR (CDCl$_3$; 400 MHz): δ 9.61 (s, 1H), 8.36 (d, 1H, J=8.4 Hz), 7.74 (s, 1H), 7.38 (dd, 1H, J=8.4, 1.9 Hz), 7.26 (m, 1H), 5.88 (s, 1H), 3.92-3.79 (m, 4H), 2.34-2.26 (m, 4H), 2.13 (m, 1H), 1.87-1.77 (m, 4H), 1.52 (s, 3H), 1.28 (m, 1H). Mass spectrum (ESI, m/z): Calcd. for C$_{22}$H$_{24}$N$_4$O$_3$, 393.1 (M+H). found 393.1.

Example 3

4-Cyano-1H-imidazole-2-carboxylic acid [2-(4,4-dimethyl-cyclohex-1-enyl)-6-(2-methyl-oxazolidin-2-yl)-pyridin-3-yl]-amide

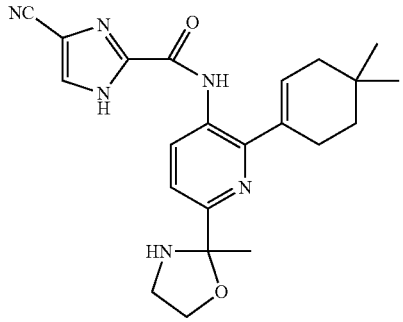 [SMILES: CC1(C)CC=C(c2nc(C3(C)NCCO3)ccc2NC(=O)c2nc(C#N)c[nH]2)CC1]

a) 6-Bromo-2-iodo-pyridin-3-ylamine

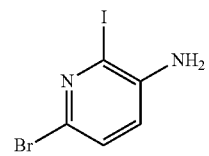

To a stirred solution of 6-bromo-pyridin-3-ylamine (10.2 g, 0.0580 mol) and Ag$_2$SO$_4$ (18.1 g, 0.0580 mol) in EtOH (150 mL) was added I$_2$ (7.59 g, 0.0580 mol) and the reaction was allowed to stir overnight. At this time hexane (200 mL) was added and the resultant mixture was filtered through Celite. The solvent was removed in vacuo, dissolved in CHCl$_3$ (200 mL), washed with aqueous saturated Na$_2$S$_2$O$_3$ (100 mL), water (1×100 mL), and dried (Na$_2$SO$_4$). The solvent was concentrated in vacuo and the residue was dissolved in hot EtOAc (100 mL), filtered and treated with hexanes (100 mL). Filtration gave 11.2 g (65%) of 6-bromo-2-iodo-pyridin-3-ylamine as a white crystalline material. $^1$H-NMR (CDCl$_3$; 400 MHz): δ 7.10 (d, 1H, J=8.2 Hz), 6.74 (d, 1H, J=8.2 Hz), 4.06 (br s, 2H).

b) 6-Bromo-2-(4,4-dimethyl-cyclohex-1-enyl)-pyridin-3-ylamine

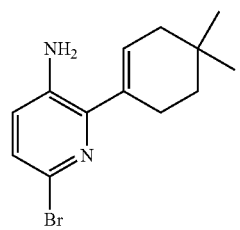 [SMILES: CC1(C)CC=C(c2nc(Br)ccc2N)CC1]

A solution of 6-bromo-2-iodo-pyridin-3-ylamine (as prepared in the previous step, 1.00 g, 3.35 mmol) in toluene (27 mL) and EtOH (13.5 mL) was treated with 2.0 M aq $Na_2CO_3$ (13.4 mL, 26.8 mmol) and 4,4-dimethyl-cyclohex-1-enylboronic acid (567 mg, 3.68 mmol). The mixture was degassed via sonication, placed under Ar, treated with $Pd(PPh_3)_4$ (271 mg, 0.234 mmol), and heated to 80° C. for 5 h. The cooled mixture was diluted with EtOAc (100 mL) and washed with water (2×50 mL). The combined aqueous layers were extracted with EtOAc (1×100 mL). The combined organic layers were dried over $MgSO_4$ and concentrated in vacuo. Silica gel chromatography of the residue on a Varian Mega-Bond Elut 50-g column with 10% EtOAc-hexane afforded 668 mg (71%) of 6-bromo-2-(4,4-dimethyl-cyclohex-1-enyl)-pyridin-3-ylamine as a tan solid. $^1$H-NMR ($CDCl_3$; 400 MHz): δ 7.06 (d, 1H, J=8.3 Hz), 6.85 (d, 1H, J=8.3 Hz), 5.95 (m, 1H), 3.86 (br s, 2H), 2.43-2.39 (m, 2H), 1.99-1.97 (m, 2H), 1.51 (t, 2H, J=6.4 Hz), 0.99 (s, 6H).

c) 4-Cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide

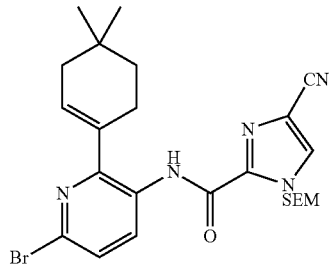 [SMILES: CC1(C)CC=C(c2nc(Br)ccc2NC(=O)c2nc(C#N)cn2COCC[Si](C)(C)C)CC1]

The title compound was prepared from 6-bromo-2-(4,4-dimethyl-cyclohex-1-enyl)-pyridin-3-ylamine (as prepared in the previous step, 60 mg, 0.21 mmol), potassium 4-cyano-1-(2-trimethylsilanyl-ethoxymethyl)-1H-imidazole-2-carboxylate (as prepared in Example 1, step (d), 91.0 mg, 0.290 mmol), PyBroP (157 mg, 0.330 mmol) and DIEA (91.0 μL, 0.520 mmol) according to the procedure in Example 1, step (f) (84 mg, 78%). $^1$H-NMR ($CDCl_3$; 400 MHz): δ 9.91 (s, 1H), 8.64 (d, 1H, J=8.6 Hz), 7.79 (s, 1H), 7.38 (d, 1H, J=8.6 Hz), 6.00 (m, 1H), 5.92 (s, 2H), 3.67 (m, 2H), 2.46 (m, 2H), 2.14 (m, 2H), 1.62 (t, 2H, J=6.3 Hz), 1.12 (s, 6H), 0.98 (m, 2H).

d) 4-Cyano-1-(2-trimethylsilanyl-ethoxymethyl)-1H-imidazole-2-carboxylic acid [2-(4,4-dimethyl-cyclohex-1-enyl)-6-(1-ethoxy-vinyl)-pyridin-3-yl]-amide

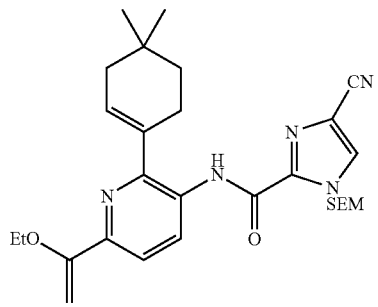 [SMILES: C=C(OCC)c1ccc(NC(=O)c2nc(C#N)cn2COCC[Si](C)(C)C)c(C2=CCC(C)(C)CC2)n1]

To a round bottom flask containing 4-cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide (as prepared in the previous step, 32 mg, 0.060 mmol), $Pd(PPh_3)_4$ (7 mg, 0.006 mmol), and tributyl-(1-ethoxy-vinyl)-stannane (30 mg, 0.080 mmol) was added DMF (0.7 mL) and the resultant solution was allowed to stir at 100° C. overnight. The reaction was diluted with EtOAc (25 mL), washed with water (2×25 mL), dried ($Na_2SO_4$) and concentrated in vacuo. Purification of the residue by preparative TLC (20% EtOAc-hexanes) afforded 12 mg (43%) of the title compound as an oil. Mass spectrum (ESI, m/z): Calcd. for $C_{28}H_{39}N_5O_3Si$, 522.2 (M+H). found 522.3.

b) 5-Cyano-1H-imidazole-2-carboxylic acid [6-acetyl-2-(4,4-dimethyl-cyclohex-1-enyl)-pyridin-3-yl]-amide

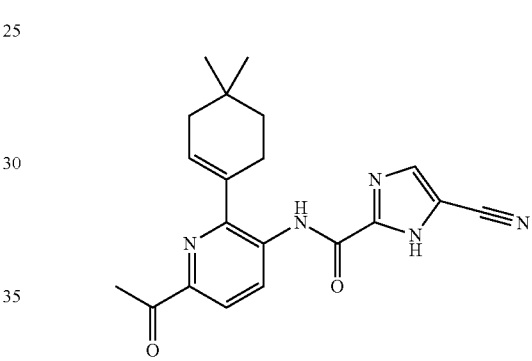

The title compound was prepared from 5-cyano-1-(2-trimethylsilanyl-ethoxymethyl)-1H-imidazole-2-carboxylic acid [2-(4,4-dimethyl-cyclohex-1-enyl)-6-(1-ethoxy-vinyl)-pyridin-3-yl]-amide (as prepared in the previous step, 12 mg, 0.023 mmol)) as a solution in 10 mL of DCM with 0.4 mL of EtOH and 10 mL of TFA; the mixture was stirred for 1 h at RT. The mixture was concentrated and triturated with $Et_2O$ to give (4.4 mg, 52%). Mass spectrum (ESI, m/z): Calcd. for $C_{20}H_{21}N_5O_2$, 364.1 (M+H). found 364.1.

c) 4-Cyano-1H-imidazole-2-carboxylic acid [2-(4,4-dimethyl-cyclohex-1-enyl)-6-(2-methyl-oxazolidin-2-yl)-pyridin-3-yl]-amide The title compound is prepared from 5-cyano-1H-imidazole-2-carboxylic acid [6-acetyl-2-(4,4-dimethyl-cyclohex-1-enyl)-pyridin-3-yl]-amide (as prepared in the previous step) and 2-aminoethanol according to the procedure in Example 1, step (h).

The following examples are produced according to procedures of previous examples with the corresponding reagents as indicated in the table below:

| Example No. | Name | Structure | Procedure Reference | Reagents |
|---|---|---|---|---|
| 4 | 4-Cyano-1H-imidazole-2-carboxylic acid [2-(4,4-dimethyl-cyclohex-1-enyl)-4-(2-methyl-oxazolidin-2-yl)-phenyl]-amide | 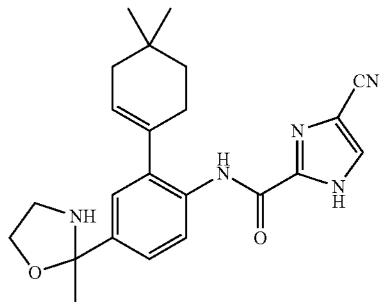 [SMILES: CC1(C)CC=C(c2cc(C3(C)NCCO3)ccc2NC(=O)c2nc(C#N)c[nH]2)CC1] | Example 1, steps (e-i) | Combi-Blocks |
| 5 | 4-Cyano-1H-imidazole-2-carboxylic acid [2-(4,4-dimethyl-cyclohex-1-enyl)-4-(2,3-dimethyl-oxazolidin-2-yl)-phenyl]-amide | 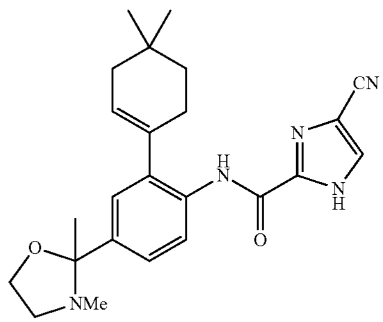 [SMILES: CN1CCOC1(C)c1ccc(NC(=O)c2nc(C#N)c[nH]2)c(C2=CCC(C)(C)CC2)c1] | Example 1, steps (e-i) | Combi-Blocks |

IV. RESULTS

Fluorescence Polarization Competition Immunoassay

An autophosphorylation, fluorescence polarization competition immunoassay was used to determine the potency for c-fms inhibition exhibited by selected compounds of Formula I. The assay was performed in black 96-well microplates (LJL BioSystems). The assay buffer used was 100 mM 4-(2-hydroxyethyl)piperazine 1-ethanesulfonic acid (HEPES), pH 7.5, 1 mM 1,4-dithio-DL-threitol (DTT), 0.01% (v/v) Tween-20. Compounds were diluted in assay buffer containing 4% dimethylsulfoxide (DMSO) just prior to the assay. To each well, 5 μL of compound were added followed by the addition of 3 μL of a mix containing 33 nM c-fms (Johnson & Johnson PRD) and 16.7 mM $MgCl_2$ (Sigma) in assay buffer. The kinase reaction was initiated by adding 2 μL of 5 mM ATP (Sigma) in assay buffer. The final concentrations in the assay were 11 nM c-fms, 1 mM ATP, 5 mM $MgCl_2$, 2% DMSO. Control reactions were ran in each plate: in positive and negative control wells, assay buffer (made 4% in DMSO) was substituted for the compound; in addition, positive control wells received 1.2 μL of 50 mM ethylene diaminetetraaceticacid (EDTA).

The plates were incubated at room temperature for 45 min. At the end of the incubation, the reaction was quenched with 1.2 μL of 50 mM EDTA (EDTA was not added to the positive control wells at this point; see above). Following a 5-min incubation, each well received 10 μL of a 1:1:3 mixture of anti-phosphotyrosine antibody, 10×, PTK green tracer, 10× (vortexed), FP dilution buffer, respectively (all from PanVera, cat. #P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. The reported $IC_{50}$ values are averages of three independent measurements.

CSF-1-Driven Mouse Bone-Marrow Derived Macrophages Assay

Macrophages are derived by culturing mouse bone marrow in alpha-MEM supplemented with 10% FCS and 50 ng/ml recombinant mouse CSF-1 in bacteriologic dishes. On the sixth day, macrophages are detached from dishes, washed, and resuspended to 0.05 million cells/ml in alpha-MEM containing 10% FCS. One hundred ul of cell suspension are distributed per well into 96 well culture plates. Wells are further supplemented with the addition of 50 ul media containing 15 ng/ml CSF-1, 3 uM Indomethacin, and 3× of a dilution series of test compounds. The cells are cultured for 30 hrs at 37 degrees and 5% CO2. During the final six hours, cultures are supplemented with an additional 30 ul of media containing a 1:500 dilution of bromodeoxyuridine (BrDU). At the end of the culture period, the plates are spun at 1000 RPM for 1 minute and 130 ul of media is removed with a pipet and replaced with 150 ul of fixative solution for 1 hour @ room temperature. The fixative is then dispelled from the plates and the plates allowed to air dry. Incorporation of BrDU into the fixed, dried cells is quantified using a specific ELISA.

Table 2 lists the assay results for representative compounds of the invention.

TABLE 2

| Example # | 1 nM c-fms; peptide Pi assay IC-50 (μM) | mCSF driven proliferation BMDM (Mouse) IC-50 (μM) |
|---|---|---|
| 1 | 0.0034 | 0.048 |
| 2 | 0.0039 | 0.044 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The invention claimed is:

1. A compound of Formula I

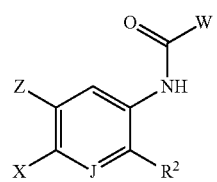

or a tautomer or pharmaceutically acceptable salt thereof, wherein:

W is

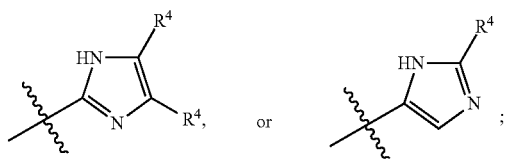

wherein each $R^4$ is independently H, F, Cl, Br, I, OH, OCH$_3$, OCH$_2$CH$_3$, SC$_{(1-4)}$alkyl, SOC$_{(1-4)}$alkyl, SO$_2$C$_{(1-4)}$alkyl, —C$_{(1-3)}$alkyl, CO$_2$R$^d$, CONR$^e$R$^f$, C≡CR$^g$, or CN;
  wherein R$^d$ is H, or —C$_{(1-3)}$alkyl;
  R$^e$ is H, or —C$_{(1-3)}$alkyl;
  R$^f$ is H, or —C$_{(1-3)}$alkyl; and
  R$^g$ is H, —CH$_2$OH, or —CH$_2$CH$_2$OH;

$R^2$ is cycloalkyl, spiro-substituted cycloalkenyl, or phenyl, any of which may be independently substituted with one or two of each of the following: chloro, fluoro, hydroxy, C$_{(1-3)}$alkyl, and C$_{(1-4)}$alkyl;

Z is H, F, or CH$_3$;

J is N;

X is

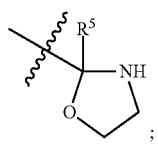

$R^5$ is H, —C$_{(1-6)}$alkyl, —OC$_{(1-4)}$alkyl, —CN, —NA$^3$A$^4$, —SO$_2$CH$_3$, —CO$_2$C$_{(1-4)}$alkyl, —CH$_2$—NA$^3$A$^4$, —CH$_2$CH$_2$NA$^3$A$^4$, —CONA$^3$A$^4$, —CH$_2$OC$_{(1-4)}$alkyl, —OC$_{(1-4)}$alkylOR$^a$, —NHCH$_2$CH$_2$CO$_2$C$_{(1-4)}$alkyl, —NHCH$_2$CH$_2$OC$_{(1-4)}$alkyl, —N(C$_{(1-4)}$alkyl)CH$_2$CH$_2$NA$^3$A$^4$, —OC$_{(1-4)}$alkylNA$^3$A$^4$, —OCH$_2$CO$_2$C$_{(1-4)}$alkyl, —CH$_2$CO$_2$C$_{(1-4)}$alkyl, —CH$_2$CH$_2$SO$_2$C$_{(1-4)}$alkyl, —SO$_2$CH$_2$CH$_2$NA$^3$A$^4$, —SOCH$_2$CH$_2$NA$^3$A$^4$, —SCH$_2$CH$_2$NA$^3$A$^4$, —NHSO$_2$CH$_2$CH$_2$NA$^3$A$^4$, phenyl;

$A^3$ is —C$_{(1-4)}$alkyl, or CH$_2$CH$_2$OR$^a$; and $A^4$ is —C$_{(1-4)}$alkyl, COR$^a$, CH$_2$CON(CH$_3$)$_2$, —CH$_2$CH$_2$OR$^a$, —CH$_2$CH$_2$SC$_{(1-4)}$alkyl, —CH$_2$CH$_2$SOC$_{(1-4)}$alkyl, or —CH$_2$CH$_2$SO$_2$C$_{(1-4)}$alkyl.

2. The compound of claim 1, wherein:

W is

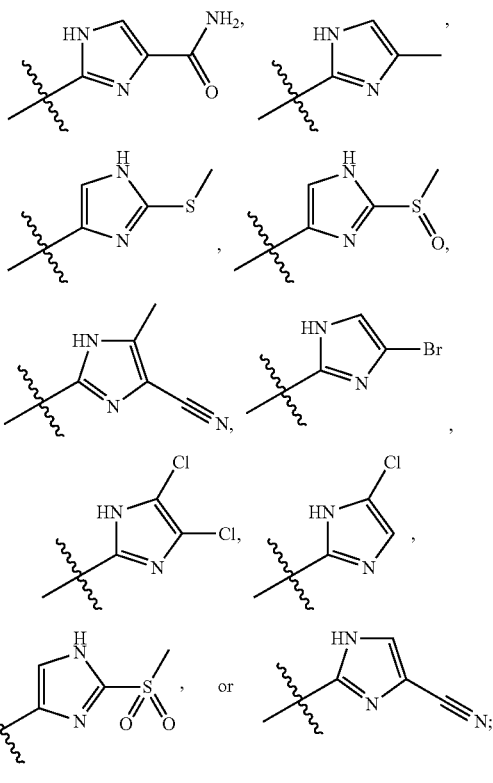

$R^2$ is

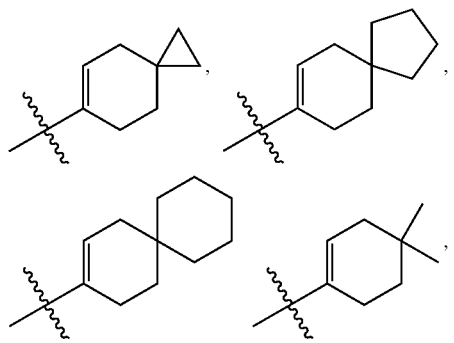

-continued

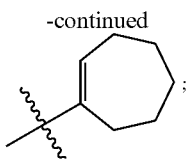

X is

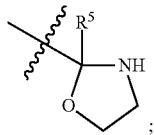

$R^5$ is H, —$C_{(1-6)}$alkyl, phenyl, —$CH_2CH_2NA^3A^4$, —$CH_2CH_2SO_2CH_3$, —$CH_2NA^3A^4$, or —$CH_2OR^a$;
wherein:
$A^3$ is —$CH_3$;
$A^4$ is —$COCH_3$, or —$CH_3$; and
$R^a$ is H, or —$C_{(1-4)}$alkyl;
or a tautomer or pharmaceutically acceptable salt thereof.

3. The compound of claim 2, wherein:
$R^2$ is

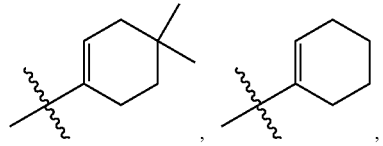

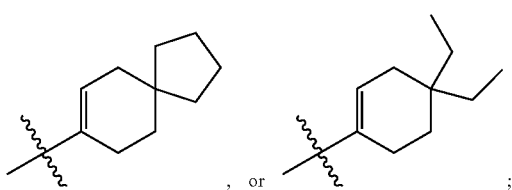

X is

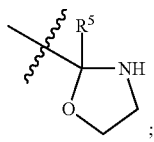

$R^5$ is —$C_{(1-3)}$alkyl, —$CH_2NA^3A^4$, or —$CH_2OR^a$;
wherein:
$A^3$ is —$CH_3$;
$A^4$ is —$COCH_3$, or —$CH_3$; and
$R^a$ is H, or —$C_{(1-4)}$alkyl;
or a tautomer or pharmaceutically acceptable salt thereof.

4. The compound of claim 3, wherein:
W is

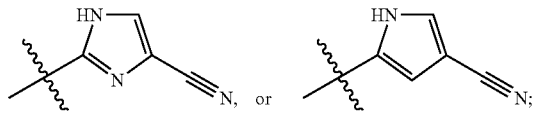 [SMILES: *c1nc(C#N)c[nH]1 ; *c1cc(C#N)c[nH]1]

$R^2$ is

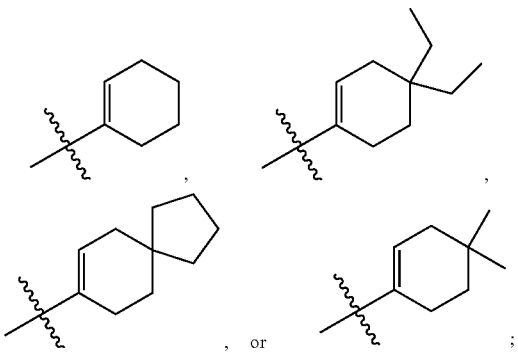

X is

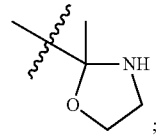

or a tautomer or pharmaceutically acceptable salt thereof.

5. The compound of Formula I

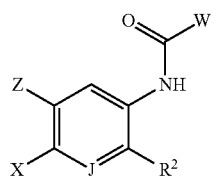

or a tautomer or pharmaceutically acceptable salt thereof, wherein:
W is

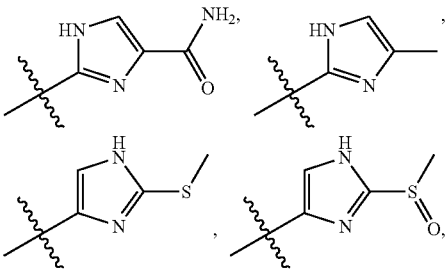

-continued

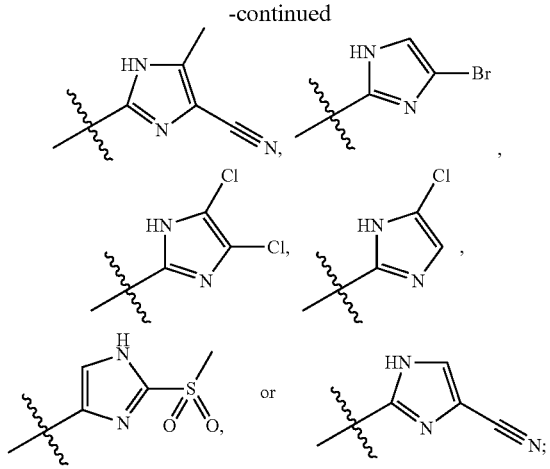

R² is

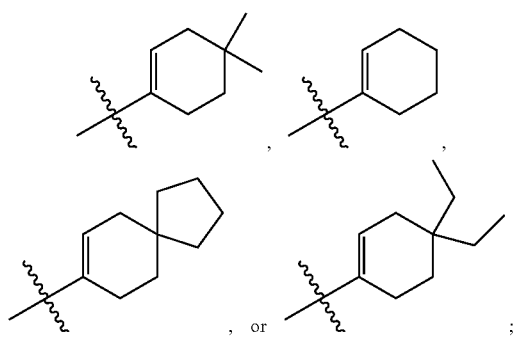

Z is H;
J is N;
X is

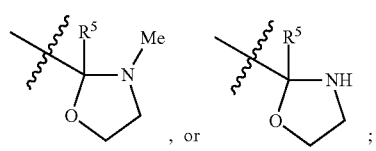

R⁵ is —C$_{(1-3)}$alkyl, —CH$_2$NA³A⁴, or —CH$_2$OR$^a$;
wherein:
A³ is —CH$_3$;
A⁴ is —COCH$_3$, or —CH$_3$; and
R$^a$ is H, C$_{(1-4)}$alkyl.

6. The compound selected from the group consisting of:

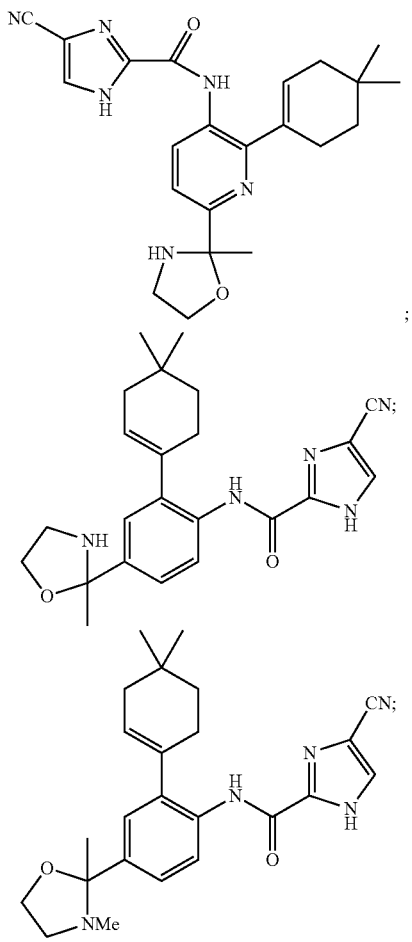

or a tautomer pharmaceutically acceptable salt thereof.

7. A pharmaceutical composition, comprising a compound of claim 1 and a pharmaceutically acceptable carrier.

8. A pharmaceutical dosage form comprising a pharmaceutically acceptable carrier and from about 0.5 mg to about 10 g of at least one compound of claim 1.

9. The dosage form of claim 8 adapted for parenteral or oral administration.

* * * * *